(12) United States Patent
Tam et al.

(10) Patent No.: US 11,123,389 B2
(45) Date of Patent: Sep. 21, 2021

(54) PHYTOESTROGEN PRODUCT OF RED CLOVER AND PHARMACEUTICAL USES THEREOF

(71) Applicant: Sinoveda Canada Inc., Edmonton (CA)

(72) Inventors: Yun Kau Tam, Edmonton (CA);
Yi-Chan James Lin, Edmonton (CA);
Brian Duff Sloley, Edmonton (CA);
Chih-Yuan Tseng, Edmonton (CA)

(73) Assignee: MAIN HARBOUR BIOTECH INTERNATIONAL LIMITED, Hong Kong (CN)

( * ) Notice: Subject to any disclaimer, the term of this patent is extended or adjusted under 35 U.S.C. 154(b) by 0 days.

(21) Appl. No.: 16/376,044

(22) Filed: Apr. 5, 2019

(65) Prior Publication Data
US 2019/0247454 A1   Aug. 15, 2019

Related U.S. Application Data

(60) Division of application No. 15/149,183, filed on May 9, 2016, now Pat. No. 10,307,451, which is a continuation-in-part of application No. 14/242,981, filed on Apr. 2, 2014, now Pat. No. 9,333,192, which is a continuation-in-part of application No. PCT/IB2012/055277, filed on Oct. 2, 2012, and a continuation-in-part of application No. 14/069,740, filed on Nov. 1, 2013, now abandoned, which is a continuation of application No. 13/251,267, filed on Oct. 2, 2011, now abandoned, which is a continuation-in-part of application No. 13/028,136, filed on Feb. 15, 2011, now abandoned.

(60) Provisional application No. 61/542,253, filed on Oct. 2, 2011, provisional application No. 61/304,589, filed on Feb. 15, 2010.

(51) Int. Cl.
| | |
|---|---|
| *A61K 36/48* | (2006.01) |
| *G16H 50/50* | (2018.01) |
| *A61K 31/353* | (2006.01) |
| *A61K 31/352* | (2006.01) |
| *G16C 20/30* | (2019.01) |

(52) U.S. Cl.
CPC ............ *A61K 36/48* (2013.01); *A61K 31/352* (2013.01); *A61K 31/353* (2013.01); *G16H 50/50* (2018.01); *G16C 20/30* (2019.02)

(58) Field of Classification Search
CPC ......... H01L 43/08; H01L 43/10; H01L 43/12; H01L 27/228
See application file for complete search history.

(56) References Cited

U.S. PATENT DOCUMENTS

2008/0038387 A1* 2/2008 Kelly .................... A61K 31/35
                                                       424/757

OTHER PUBLICATIONS

Tsao et al., J Agric. Food Chem. 2006, 54, 57978-5805. (Year: 2006).*

* cited by examiner

*Primary Examiner* — Jean P Cornet
(74) *Attorney, Agent, or Firm* — Law Offices of Albert Wai-Kit Chan, PLLC

(57) ABSTRACT

The present invention provides compositions comprising optimized ratios of Red clover phytoestrogens as determined by a proprietary physiologically based pharmacokinetic and pharmacodynamic model. The compositions are useful for modulating, preventing or treating postmenopausal or climacteric symptoms, which include but are not limited to bone loss, bone remodeling, hot flushes and vaginal atrophy. The present invention also provides methods for modulating, preventing or treating postmenopausal or climacteric symptoms using the compositions disclosed herein.

8 Claims, 15 Drawing Sheets

PHYTOESTROGEN PRODUCT OF RED CLOVER AND PHARMACEUTICAL USES THEREOF

CROSS-REFERENCE TO RELATED APPLICATIONS

This application is a continuation application of U.S. application Ser. No. 15/149,183, filed May 9, 2016, which is continuation-in-part application of U.S. application Ser. No. 14/242,981, filed Apr. 2, 2014, which is a continuation-in-part application of International App'l No. PCT/IB2012/055277, filed Oct. 2, 2012, which claims benefit of U.S. App'l No. 61/542,253, filed Oct. 2, 2011; U.S. application Ser. No. 14/242,981 also is a continuation-in-part application of U.S. application Ser. No. 14/069,740, filed Nov. 1, 2013, which is a continuation of U.S. application Ser. No. 13/251,267, filed Oct. 2, 2011, which is a continuation-in-part of U.S. application Ser. No. 13/028,136, filed Feb. 15, 2011, which claims the benefit of U.S. App'l No. 61/304,589, filed Feb. 15, 2010. The entire contents of the preceding applications are incorporated herein by reference into this application.

BACKGROUND OF THE INVENTION

Deficiency of estrogens during menopause can lead to a number of complications including hot flushes, reduced bone density, mood swings, vaginal atrophy, etc. These symptoms are commonly treated with synthetic hormones. Although postmenopausal symptoms can be alleviated, hormone replacement therapy (HRT) was discovered to be associated with increased cardiovascular disorders in one of the largest studies of its kind (Women's health Initiative, WHI) (Seelig, Altura et al. 2004). HRT was also linked to increased risk of breast and ovarian cancer (Fernandez, Gallus et al. 2003, Gambacciani, Monteleone et al. 2003). After the WHI trial results were published, the use of HRT was reduced dramatically. Many postmenopausal women have resorted to alternative therapy because phytoestrogens are generally considered to be safe and efficacious. The use of soy and Red clover; the most common species used is *Trifolium pratense*, which are rich in phytoestrogens, has been on the rise (Beck, Rohr et al. 2005). Despite the trend, clinical trial results on phytoestrogens, however, have been equivocal. For example, the effects of Red clover on postmenopausal bone loss have been marginal (Beck, Rohr et al. 2005, Booth, Piersen et al. 2006, Wuttke, Jarry et al. 2007, Ma, Qin et al. 2008, Lagari and Levis 2014). Despite occasional success, a large percentage of clinical trials showed no significant effects on postmenopausal bone loss. Similar data have been obtained for other postmenopausal symptoms such as hot flashes (Ghazanfarpour, Sadeghi et al. 2015, Ghazanfarpour, Sadeghi et al. 2016) and vaginal atrophy (Ghazanfarpour, Latifnejad Roudsari et al. 2015, Ghazanfarpour, Sadeghi et al. 2016). Alternative therapy has not replaced HRT effectively. A recent study showed that the trend of women moving away from HRT has led to an alarming increase in bone fractures and it is estimated that fractures related to menopause is expected to exceed 40,000 per year in women aged 65-69 years (Gambacciani, Ciaponi et al. 2007). Since the side effects of HRT were publicized after the WHI trial, it has since been reevaluated. There is no consensus with regard to HRT's safety among the medical research community. Therefore, a much closer look at the 'less than expected' effects of phytoestrogens should be undertaken because the toxicity profile of this type of products is so much more favorable.

Besides HRT, there are no drugs that could be used effectively for treating climacteric symptoms such as hot flashes and vaginal atrophy. Anti-depressants like Prozac, Paxil or Effexor, blood pressure medications like clonidine, anti-seizure drugs like gabapentin, and a paroxetine formula Brisdelle have been used for treating hot flashes. However, these drugs produce significant side effects, and the efficacy is at best marginal. Ospemifene, a selective estrogen receptor modulator, has been approved for the treatment of vaginal atrophy. However, its long term safety has not been ascertained. Genistein, a soy isoflavone has been shown to have some positive effects on vaginal cell structure.

The major bioactive isoflavones in soy are genistein, daidzein, glycitein and prunetin (Setchell and Cassidy 1999). They are also present in their glycoside forms. There are three classes of bioactives in red clover: isoflavones, coumestrols and lignans (Beck, Rohr et al. 2005). The quantity of coumestrols and lignans is small; therefore, their contribution to the overall activity is likely minimal. The major isoflavones in red clover are Biochanin A and formononetin (Liu, Burdette et al. 2001, Overk, Yao et al. 2005, Booth, Overk et al. 2006). Genistein and daidzein are present in minute quantities. Biochanin A and formononetin are precursors of their respective active moieties, genistein and daidzein. The conversion takes place in the intestine by intestinal flora and liver, although the relative significance has not been established. Daidzein is converted by bacteria in the colon to form a more estrogenic metabolite, equol. In Red clover, a significant quantity of Biochanin A and formononetin is in the form of glycosides. The glycosides in soy and red clover are converted to their respective aglycones by the intestinal flora before absorption (Setchell and Cassidy 1999).

Relative absorption of isoflavone glycoside and their respective aglycones is a subject of controversy. Although the cause of controversy is not readily apparent, the low solubility of the aglycones in a preparation may have a profound effect on their dissolution, metabolism and absorption.

Formononetin and Biochanin A are de-methylated by the intestinal micro flora to produce two active metabolites daidzein and genistein, respectively (Hur and Rafii 2000). However, the site of this metabolic pathway is questioned (Tolleson, Doerge et al. 2002).

Metabolism of isoflavones is mainly mediated by Phase II enzymes in the enterocytes and hepatocytes. Although metabolism of individual isoflavones in rats has been well characterized (Jia, Chen et al. 2004, Chen, Lin et al. 2005, Chen, Wang et al. 2005), interaction between components has not been evaluated.

Clinical studies showed that extracts of red clover or soy are safe; however, their efficacies are equivocal (Booth, Piersen et al. 2006, Lagari and Levis 2014). Although there are proprietary products in the market, which have shown potentials for treating or preventing postmenopausal osteoporosis, hot flushes and vaginal atrophy; these products unfortunately, do not have the quality of a drug. The major shortcomings for the design of these products in the market are that they have not taken into consideration of the interplay between pharmacokinetics and pharmacodynamics. In other words, proper dosage and/or dosing interval are empirically decided.

In this invention, the interplay between these "active" components is evaluated and quantified using a proprietary physiologically based pharmacokinetic and pharmacodynamic model (PBPKPD).

One of the objectives of the present invention is to provide compositions comprising active ingredients of Red clover that are effective in modulating, preventing or treating climacteric symptoms. The compositions provided herein are formulated as special dosage forms and require a much lower dosage of phytoestrogens than Red clover products available in the market. The advantage of the present compositions is their consistency. By modifying the mode of delivery, the other advantage of the present compositions is the increase in the bioavailability of the aglycones and eliminates the conversion to their respective bioactive metabolites in the colon, which leads to variability in efficacy.

SUMMARY OF THE INVENTION

The present invention discloses compositions of active ingredients in Red clover, which are optimized to modulate, prevent or treat postmenopausal or climacteric symptoms, which include but are not limited to bone loss, bone remodeling, hot flashes and vaginal atrophy. In one embodiment, the present invention provides methods for modulating, preventing or treating postmenopausal or climacteric symptoms using the compositions disclosed herein. In one embodiment, the composition comprises at least 80% of Biochanin A, at least 1% of genistein, and no more than 5% each of formononetin and daidzein. In another embodiment, the composition is formulated as parenteral dosage forms, which include but are not limited to intravenous, intramuscular and subcutaneous delivery. In another embodiment, the composition is formulated as topical dosage forms which include but are not limited to transdermal and vaginal delivery. In another embodiment, the composition is formulated into sublingual and buccal dosage forms.

DETAILED DESCRIPTION OF THE FIGURES

Figure 5:
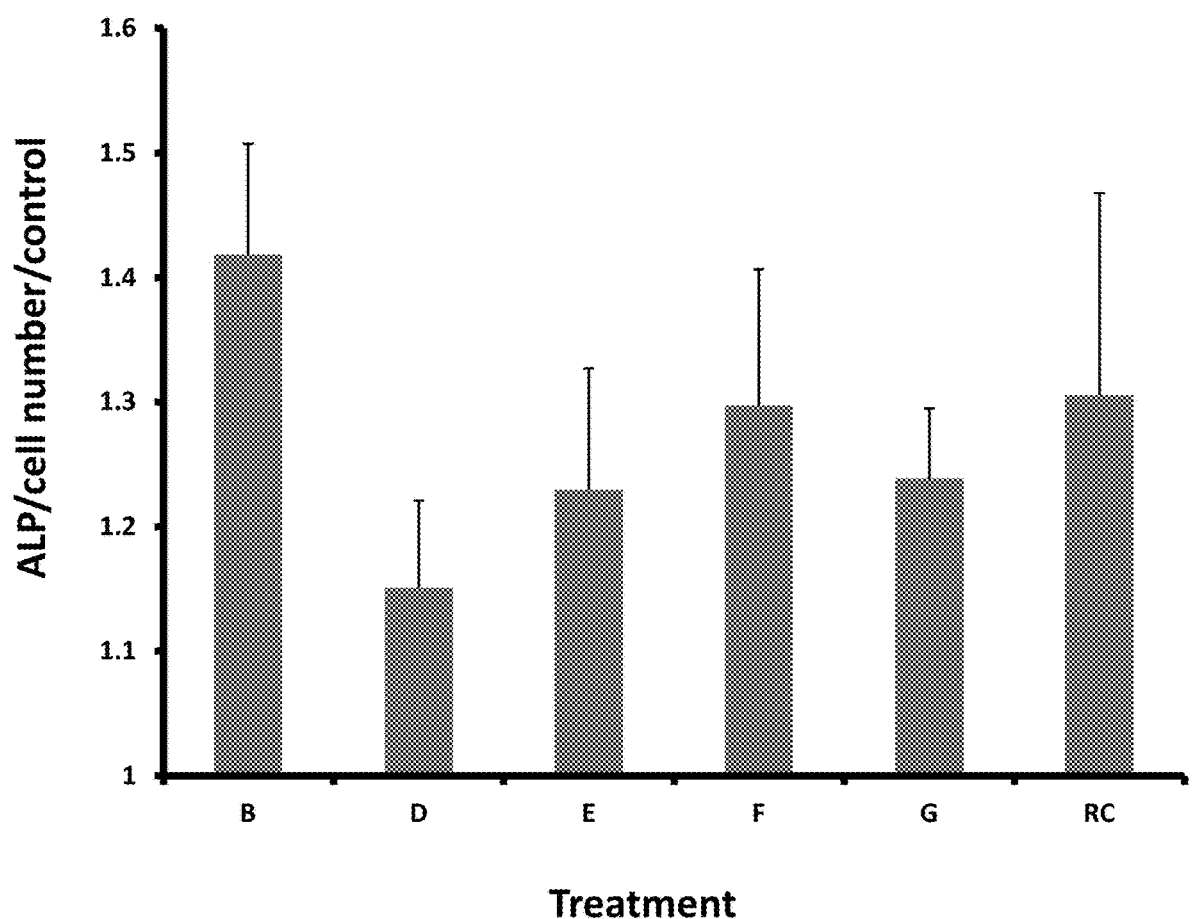

FIG. 5 shows the effects of individual Red clover isoflavones on osteoblast differentiation of MC3T3 cells. The total concentration of isoflavone in each treatment is 10 µM. B: Biochanin A; D: daidzein; E: equol; F: formononetin; G: genistein; and RC: Red clover extract. ALP/cell number ratio obtained in each treatment is normalized by the control to quantify relative osteoblast activities.

Figure 6:
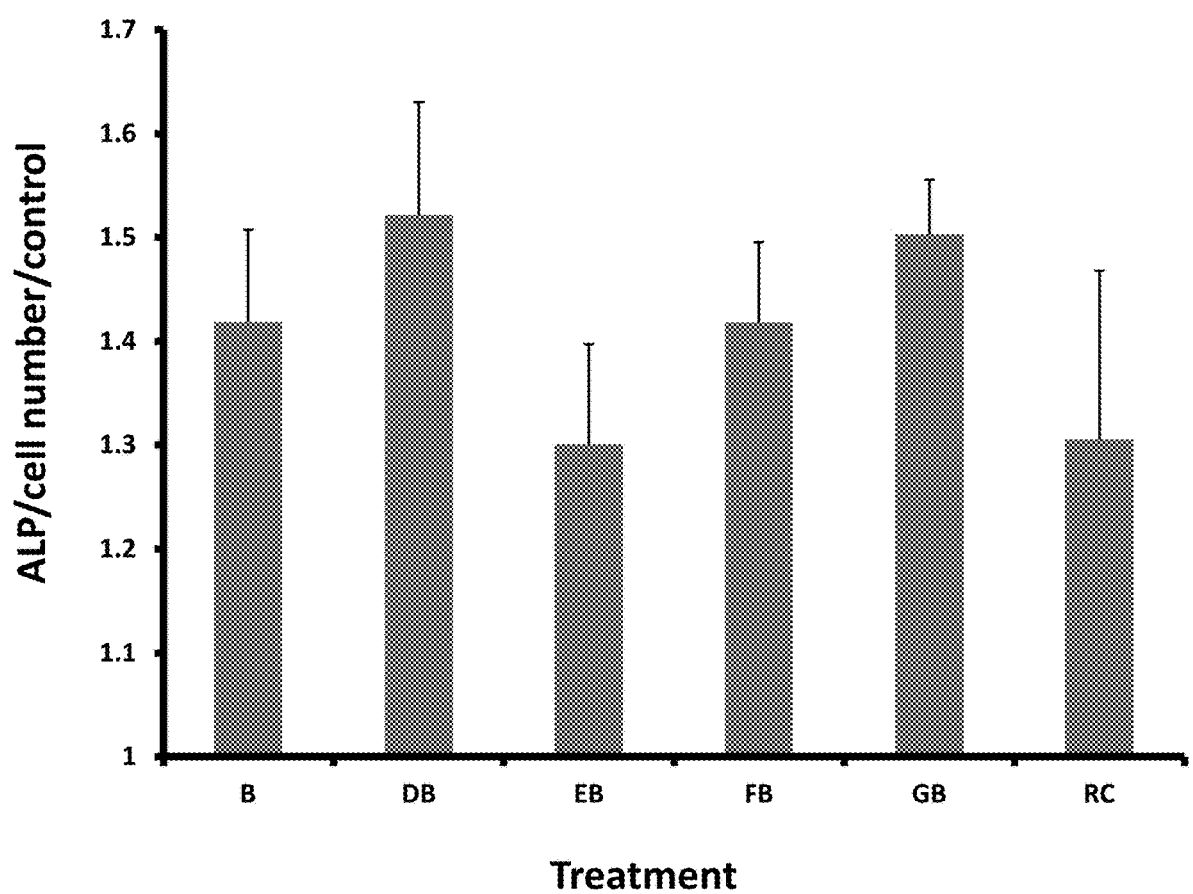

FIG. 6 shows the effects of Red clover isoflavone mixtures on osteoblast differentiation of MC3T3 cells. The total concentration of isoflavone in each treatment is 10 µM. For pair treatment, the ratio is 1:9. B is Biochanin A; DB is 1 µM of daidzein and 9 µM of Biochanin A; EB is 1 µM of equol and 9 µM of Biochanin A; FB is 1 µM of formononetin and 9 µM of Biochanin A; GB is 1 µM of genistein and 9 µM of Biochanin A; and RC is Red clover extract. ALP/cell number ratio obtained in each treatment is normalized by the control to quantify relative osteoblast activities.

Figure 7:
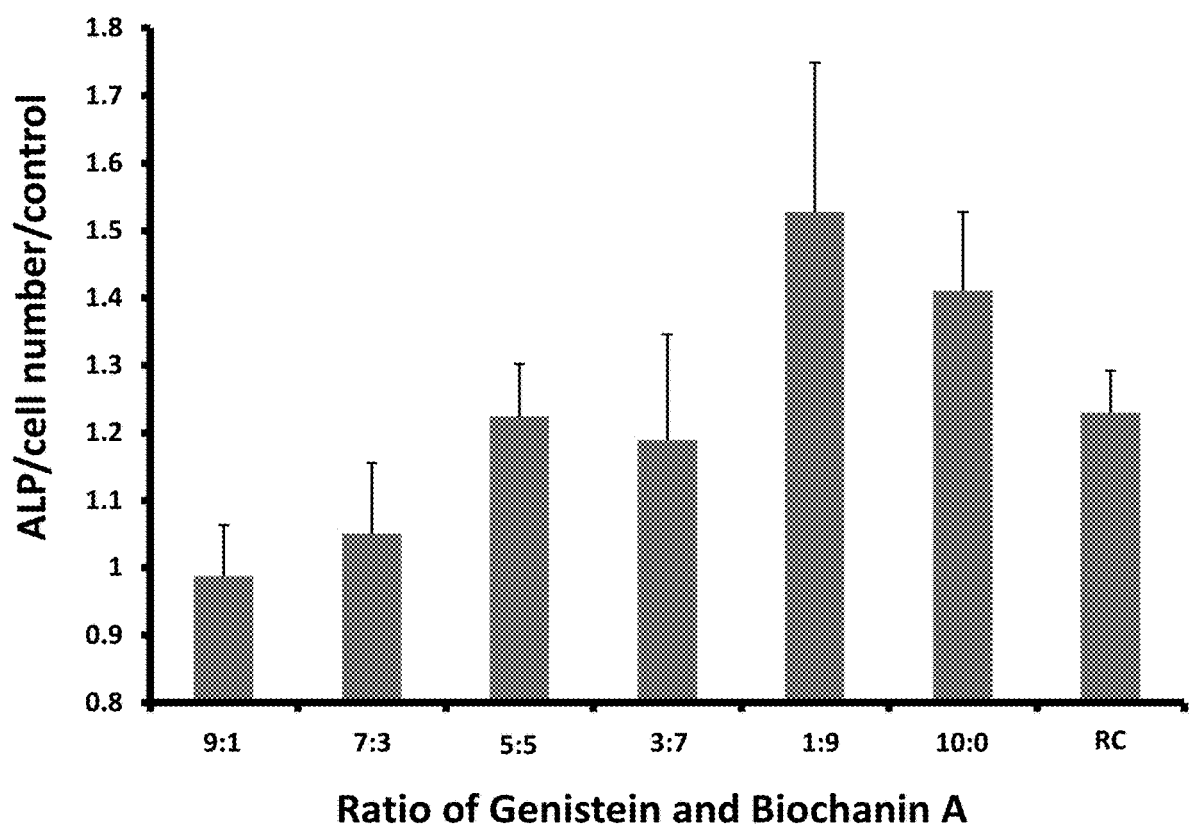

FIG. 7 shows the effects of progressive increase of genistein in a mixture of genistein and Biochanin A on the osteoblast differentiation of MC3T3 cells. The total concentration of isoflavone in each treatment is 10 µM. Effect of Red clover extract is also tested. ALP/cell number ratio obtained in each treatment is normalized by the control to quantify relative osteoblast activities.

Figure 8:
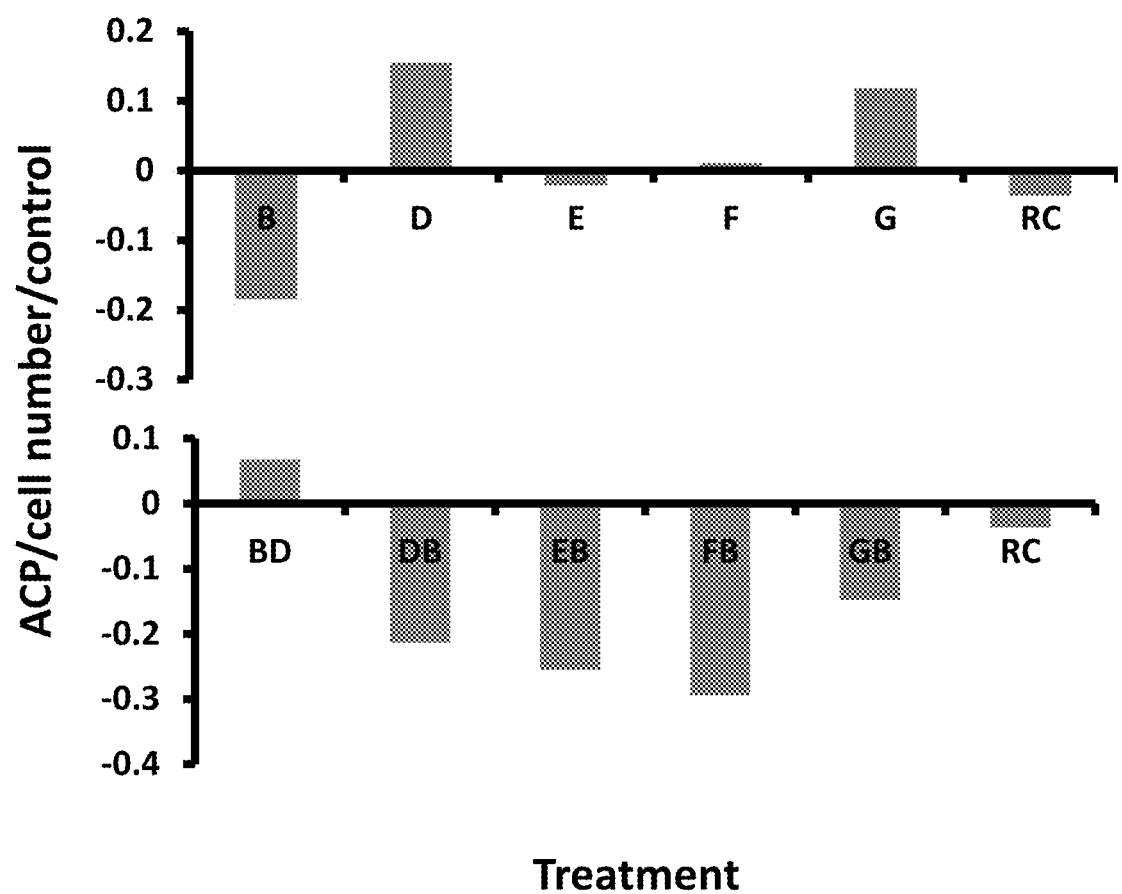

FIG. 8 shows the inhibition of osteoclast differentiation by Red clover isoflavones. The total concentration of isoflavone in each treatment is 10 µM. B: Biochanin A; D: daidzein; E: equol; F: formononetin; G: genistein; and RC: Red clover extract. For pair treatment, the ratio is 1:9. BD is 1 µM of Biochanin A and 9 µM of daidzein; DB is 1 µM of daidzein and 9 µM of Biochanin A; EB is 1 µM of equol and 9 µM of Biochanin A; FB is 1 µM of formononetin and 9 µM of Biochanin A; GB is 1 µM of genistein and 9 µM of Biochanin A; and RC is Red clover extract. ACP/cell number ratio obtained in each treatment is normalized by the control to quantify relative osteoclast activities.

Figure 9:
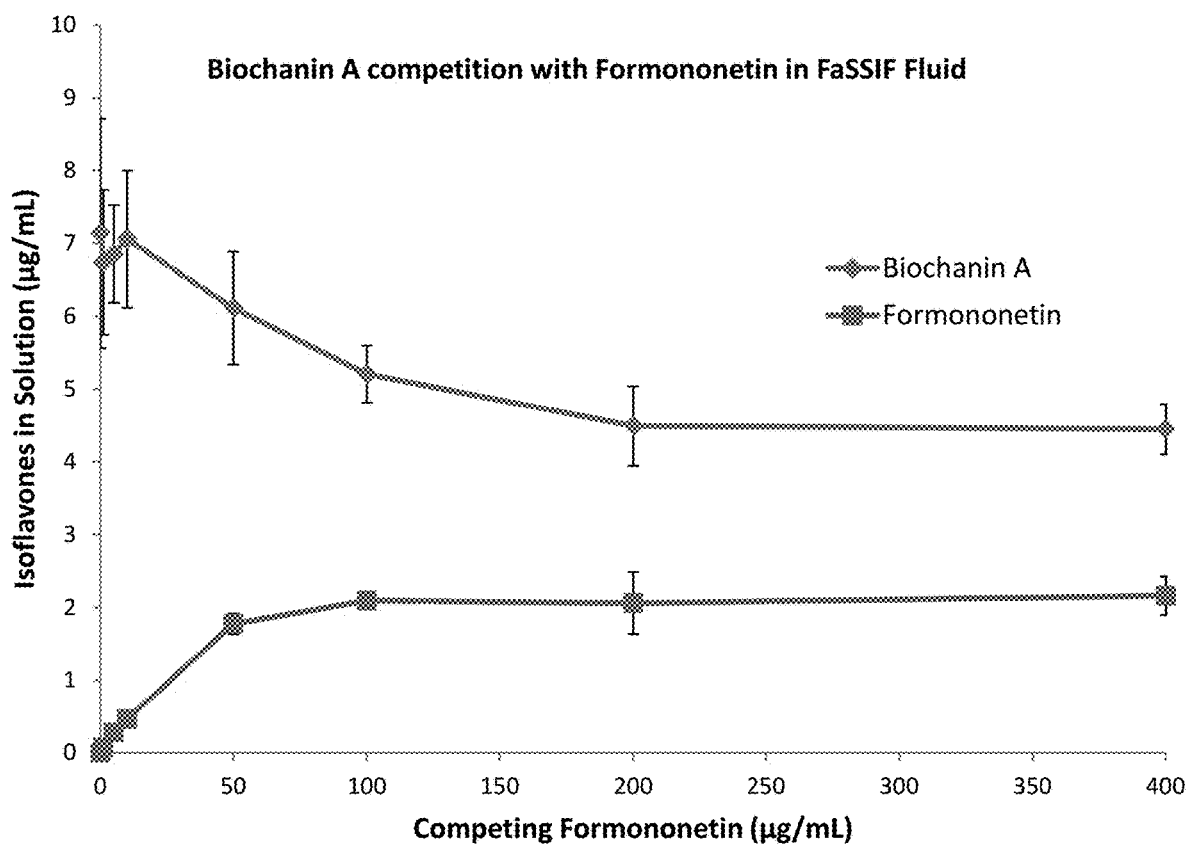

FIG. 9 shows the effects of formononetin on the solubility of Biochanin A in fasted simulated intestinal fluid (FaSSIF). The amount of Biochanin A in the mixture is 200 µg/mL.

Figure 10:
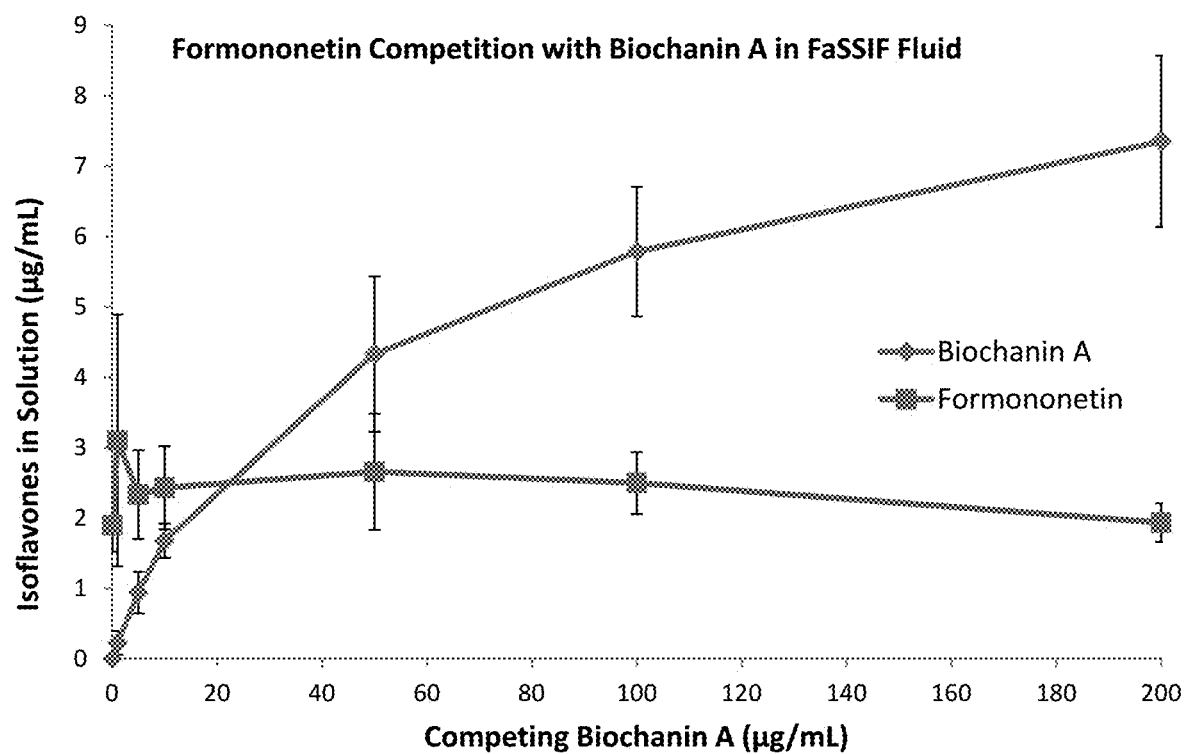

FIG. 10 shows the effects of Biochanin A on the solubility of formononetin in fasted simulated intestinal fluid (FaSSIF). The amount of formononetin in the mixture is 50 µg/mL.

Figure 11:
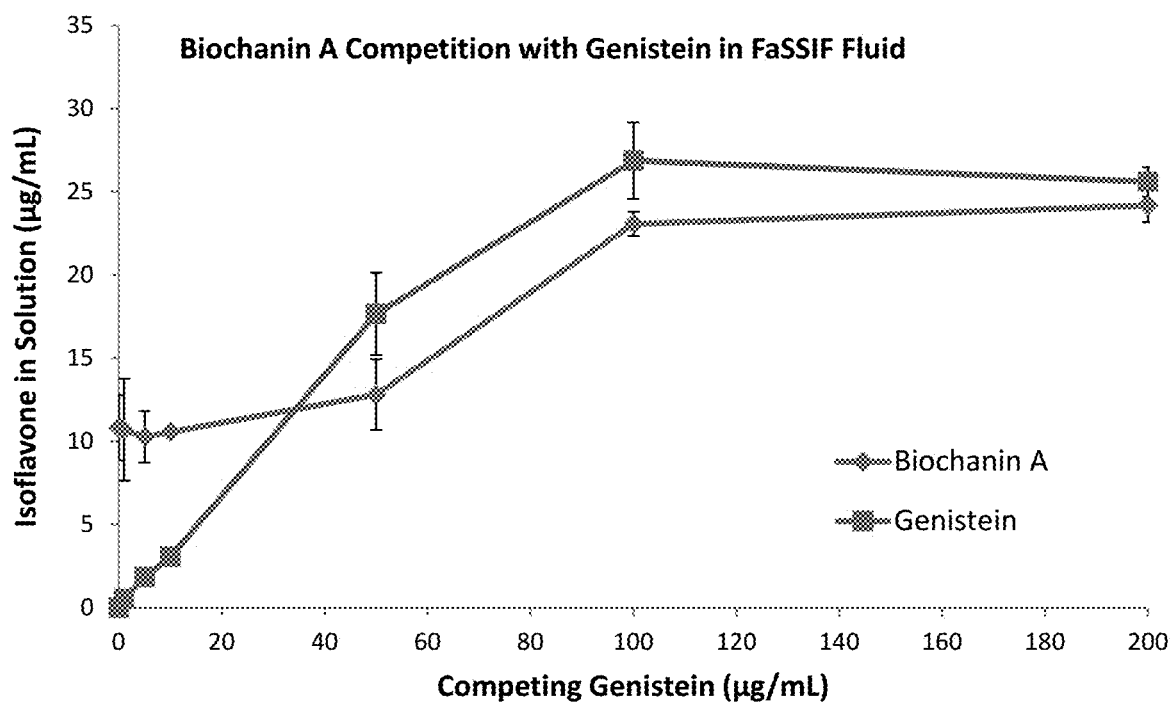

FIG. 11 shows the effects of genistein on the solubility of Biochanin A in fasted simulated intestinal fluid (FaSSIF). The amount of Biochanin A in the mixture is 200 µg/mL.

Figure 12:
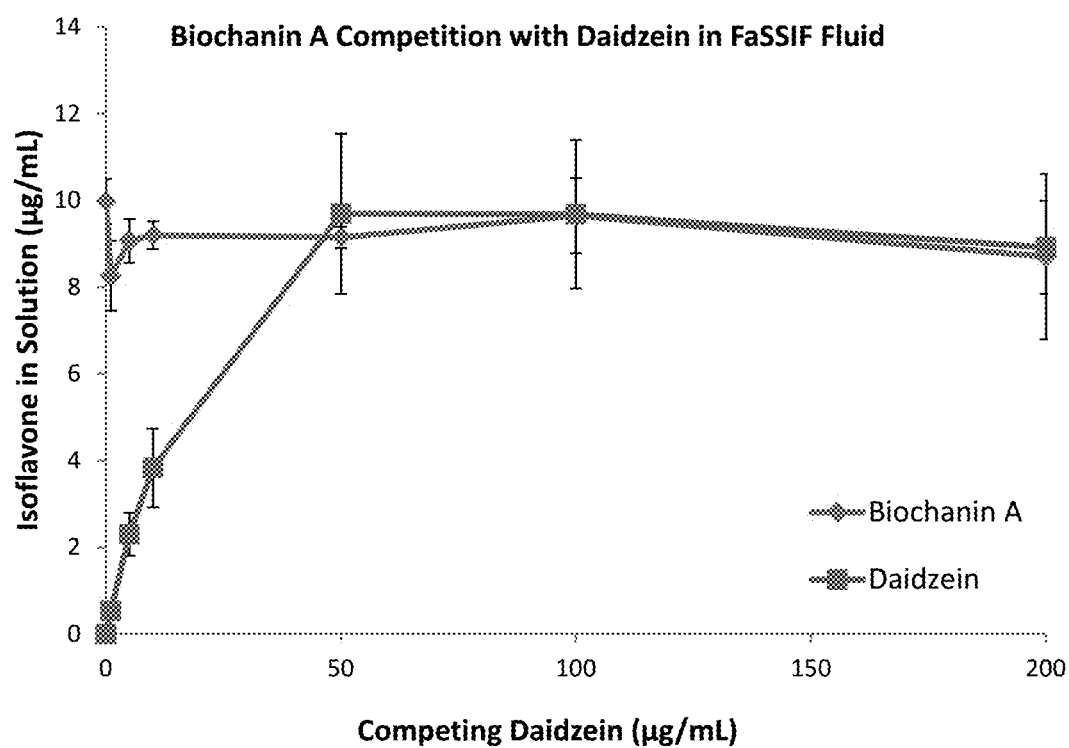
Figure 13:
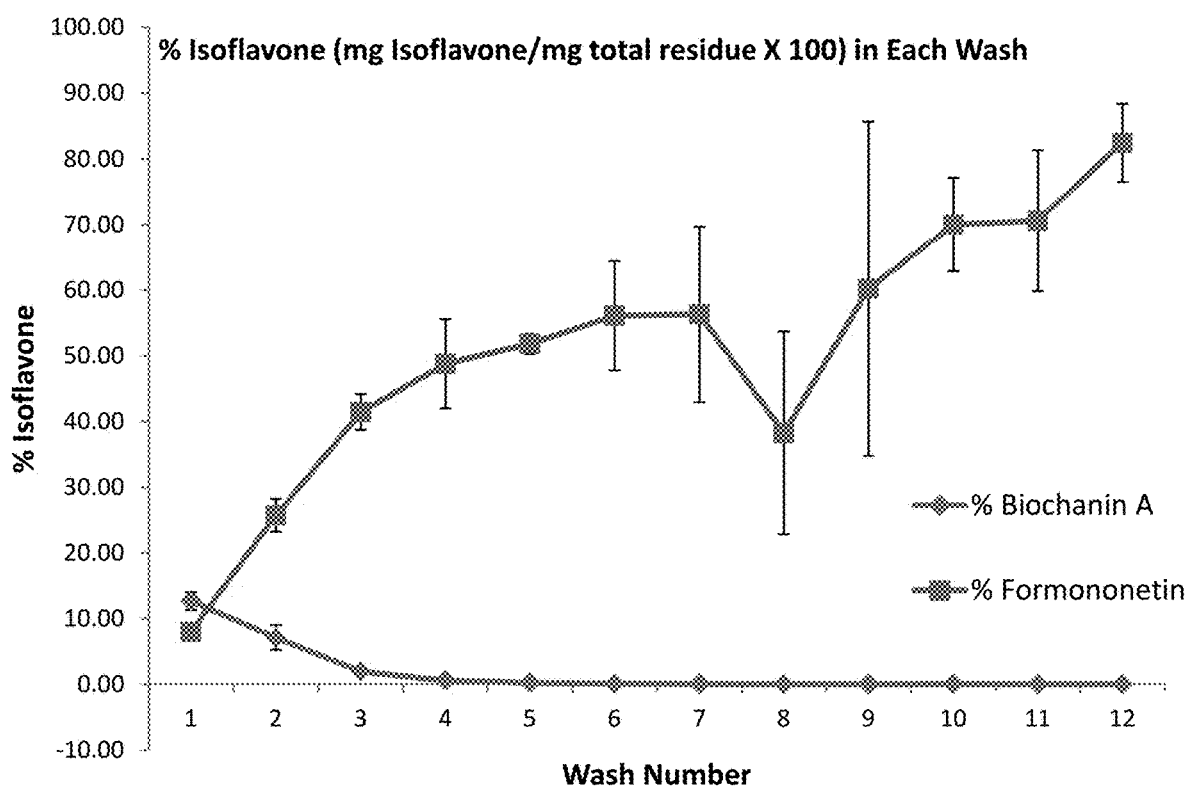

FIG. 12 shows the effects of daidzein on the solubility of Biochanin A in fasted simulated intestinal fluid (FaSSIF). The amount of Biochanin A in the mixture is 200 µg/mL FIG. 13 shows the Isoflavone profiles of a commercial Red clover extract (Shaanxi, 40% total phytoestrogen) after sequential extraction with methanol.

Figure 14:
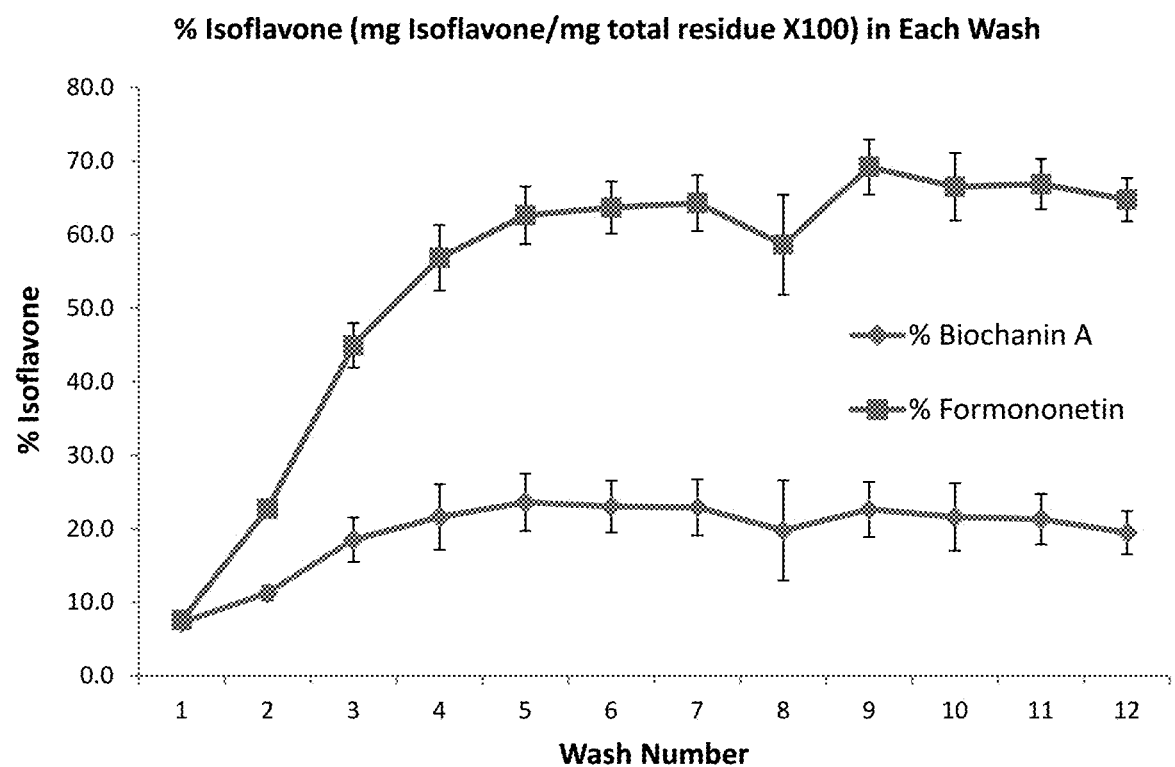

FIG. 14 shows the Isoflavone profiles of a commercial Red clover extract (Acetar, 40% total phytoestrogen) after sequential extraction with methanol.

Figure 15:
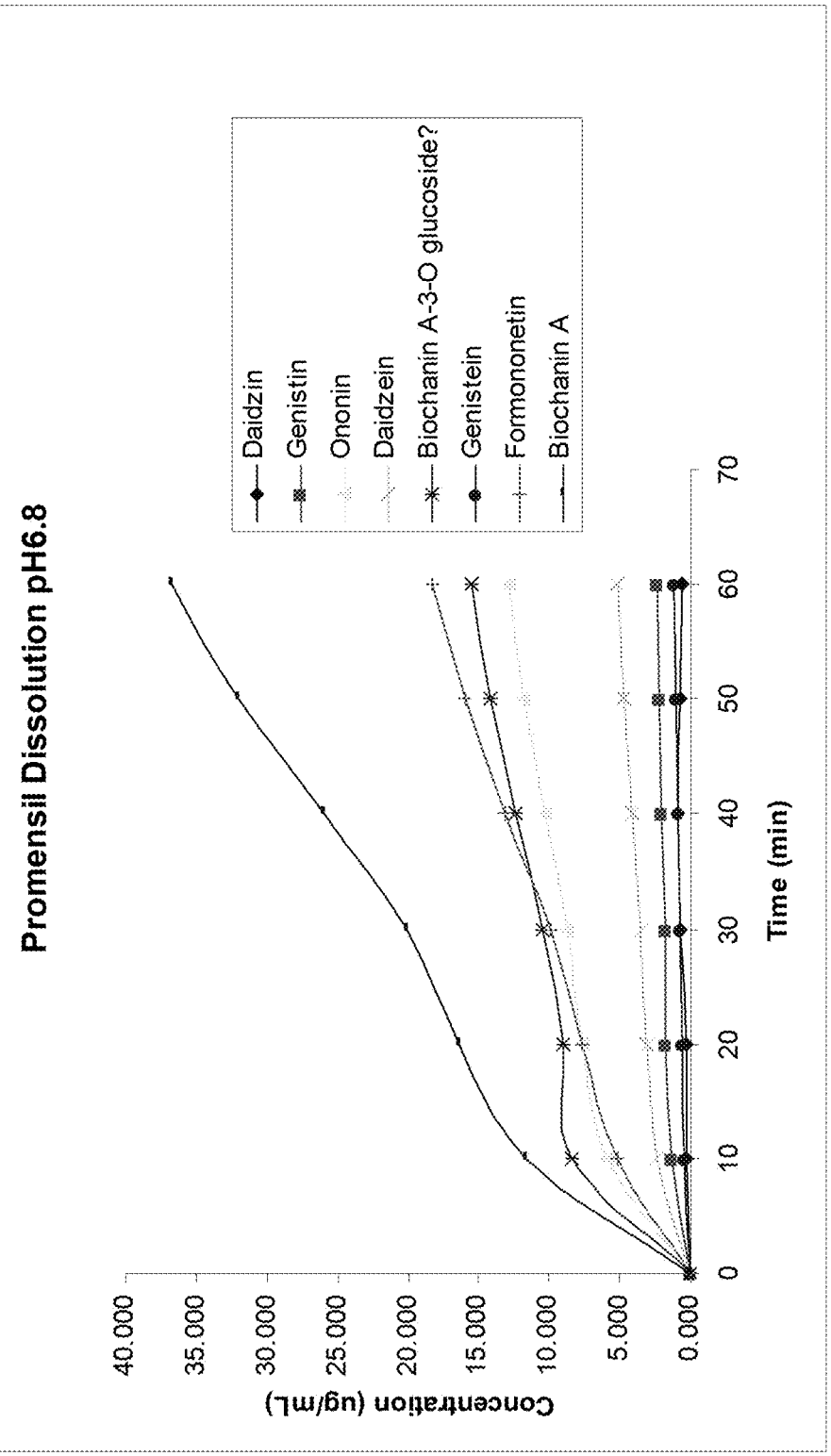

FIG. 15 shows a dissolution profile of two PROMENSIL tablets, each contains 40 mg of total phytoestrogens. The content of Biochanin A and formononetin was not completely released.

DETAILED DESCRIPTION OF THE INVENTION

Biochanin A and formononetin are the major components in Red clover. Their colonic metabolites, genistein and daidzein are also present in minute quantities (Beck, Rohr et al. 2005). A colonic metabolite of daidzein, equol, has been shown to have the highest estrogenicity among the red clover phytoestrogens (Magee 2011).

As shown below, the two major aglycones of Red clover, Biochanin A and formononetin are highly insoluble in the gastrointestinal fluids. Daidzein and genistein, two minute components in Red clover, are also insoluble, although they are more soluble than Biochanin A and formononetin.

In the present invention, Biochanin A, formononetin, daidzein and genistein are found interacting with each other at the solubility level. The presence of one phytoestrogen may enhance or inhibit the solubility of the other phytoestrogen.

Lack of solubility, high first-pass gut and liver metabolism and colonic bacteria metabolism are responsible for the highly variable and extremely low bioavailability of the active components.

In one embodiment, the present invention provides a composition comprising active ingredients in Red clover, which are optimized to reduce the rate of bone loss and severity of other climacteric conditions in postmenopausal women. In one embodiment, the composition comprises at least 80% of Biochanin A, and no more than 20% of genistein. In another embodiment, the composition comprises at least 80% of Biochanin A, and at least 1% of genistein. In one embodiment, the dose ratio of Biochanin A to genistein ranges from 4:1 to 99:1. In one embodiment, the dose ratio of Biochanin A to genistein ranges from 2:1 to 30:1. In another embodiment, the dose ratio of Biochanin A to genistein ranges from 6:1 to 9:1.

In one embodiment, the composition contains at least 80% of Biochanin A, no more than 15% of genistein, and no more than 6% each of formononetin and daidzein. In one embodiment, the composition contains at least 80% of Biochanin A, at least 1% of genistein, and no more than 5% each of formononetin and daidzein. In one embodiment, the dose ratio of Biochanin A to formononetin ranges from 5:1 to 100:1. In another embodiment, the dose ratio of Biochanin A to formononetin ranges from 16:1 to 100:1. In another embodiment, the dose ratio of Biochanin A to formononetin ranges from 20:1 to 30:1. In one embodiment, the dose ratio of Biochanin A to daidzein ranges from 5:1 to 90:1. In another embodiment, the dose ratio of Biochanin A to daidzein ranges from 16:1 to 90:1. In another embodiment, the dose ratio of Biochanin A to daidzein ranges from 18:1 to 30:1.

In one embodiment, the composition comprises a dosage of total isoflavones ranging from 0.1 to 10 mg.

In one embodiment, the compositions disclosed herein are obtained through synthetic processes, synthetic sources or natural sources.

In one embodiment, the present invention provides dosage forms of the compositions that will minimize first-pass metabolism, enhance exposure to active ingredients and minimize inter-individual variability.

In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the composition is formulated in the form of granules, injection, powder, solution, suspension, cream, foam, suppositories or capsules.

In one embodiment, the present invention provides methods of using the compositions disclosed herein for modulating bone remodeling, comprising the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention provides methods of using the compositions disclosed herein for modulating hot flashes, comprising the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention provides methods of using the compositions disclosed herein for modulating vaginal atrophy, comprising the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention provides methods of using the compositions disclosed herein for modulating one or more postmenopausal or climacteric symptoms, including but not limited to, sleep disturbances, night sweat, vaginal dryness, diaphoresis, and urinary tract symptoms. The methods comprise the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention also provides methods of using the compositions disclosed herein for treating or preventing osteoporosis, comprising the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention also provides methods of using the compositions disclosed herein for treating or preventing hot flashes, comprising the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention also provides methods of using the compositions disclosed herein for treating or preventing vaginal atrophy, comprising the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention also provides methods of using the compositions disclosed herein for treating or preventing one or more postmenopausal or climacteric symptoms, including but not limited to, sleep disturbances, vaginal dryness, diaphoresis, night sweat, and urinary tract symptoms. The methods comprise the step of administering the composition to a subject in need thereof. In one embodiment, the composition is formulated as parenteral dosage forms (such as intramuscular, subcutaneous and intravenous), buccal, sublingual, or other topical dosage forms which include but are not limited to transdermal and intra-vaginal.

In one embodiment, the present invention provides a method of modulating one or more climacteric symptoms in a subject, the method comprises the step of administering an effective amount of a composition to the subject in need thereof, and the composition comprises at least 80% of Biochanin A, at least 1% of genistein, no more than 5% of formononetin and no more than 5% of daidzein.

In one embodiment of the present method, the composition comprises no more than 15% of genistein.

In one embodiment of the present method, the ratio of Biochanin A and genistein ranges from 4:1 to 99:1. In another embodiment, the ratio of Biochanin A and formononetin ranges from 16:1 to 100:1. In another embodiment, the ratio of Biochanin A and daidzein ranges from 16:1 to 90:1.

In one embodiment of the present method, the composition comprises a dosage of total isoflavones ranging from 0.1 to 10 mg.

In one embodiment of the present method, the composition is administered via a route to avoid first-pass gastrointestinal and hepatic effects, and to avoid colonic bacterial metabolism.

In one embodiment of the present method, the composition is formulated as parenteral, buccal, sublingual, topical, transdermal or intra-vaginal dosage forms. In another embodiment, the composition is formulated as a dosage form for intramuscular, subcutaneous or intravenous administration. In another embodiment, the composition is formulated in the form of suppository, cream, injection, solution, or suspension.

In one embodiment of the present method, the climacteric symptoms comprise the following:
i) bone remodeling;
ii) bone loss;
iii) osteoporosis;
iv) hot flashes;
v) vaginal atrophy;
vi) vaginal dryness;
vii) diaphoresis;
viii) night sweat;
ix) urinary tract symptoms; and
x) sleep disturbance.

In one embodiment, the present invention provides a composition of isoflavones comprising at least 80% of Biochanin A, at least 1% of genistein, no more than 5% of formononetin and no more than 5% of daidzein.

In one embodiment of the present composition, the composition comprises no more than 15% of genistein.

In one embodiment of the present composition, the ratio of Biochanin A and genistein ranges from 4:1 to 99:1. In another embodiment, the ratio of Biochanin A and formononetin ranges from 16:1 to 100:1. In another embodiment, the ratio of Biochanin A and daidzein ranges from 16:1 to 90:1.

In one embodiment of the present composition, the composition comprises a dosage of total isoflavones ranging from 0.1 to 10 mg.

In one embodiment of the present composition, the composition is formulated as parenteral, buccal, sublingual, topical, transdermal or intra-vaginal dosage forms. In another embodiment, the composition is formulated as a dosage form for intramuscular, subcutaneous or intravenous administration. In another embodiment, the composition is formulated in the form of suppository, cream, injection, solution, or suspension.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

The objective of this study is to track the events that occur in the lumen of the gastrointestinal tract. The goals are to identify the stability of Red clover components, their physical and enzymatic stability, solubility and absorbability.

Twenty-five red clover extracts containing a diverse composition of Biochanin A, formononetin, Genistein, Daidzein and their glucosides, along with other minute quantities of coumestrols and lignans have been prepared either using solvent extraction or a variety of cultivars. In one embodiment, the aerial portion of red clovers, leaves, stems or leaves and stems, were dried powdered. The plant material was extracted with 50% ethanol at 50° C. for 1 hour. The resultant sample was centrifuged and the ethanolic component was removed and dried.

Figure 1:
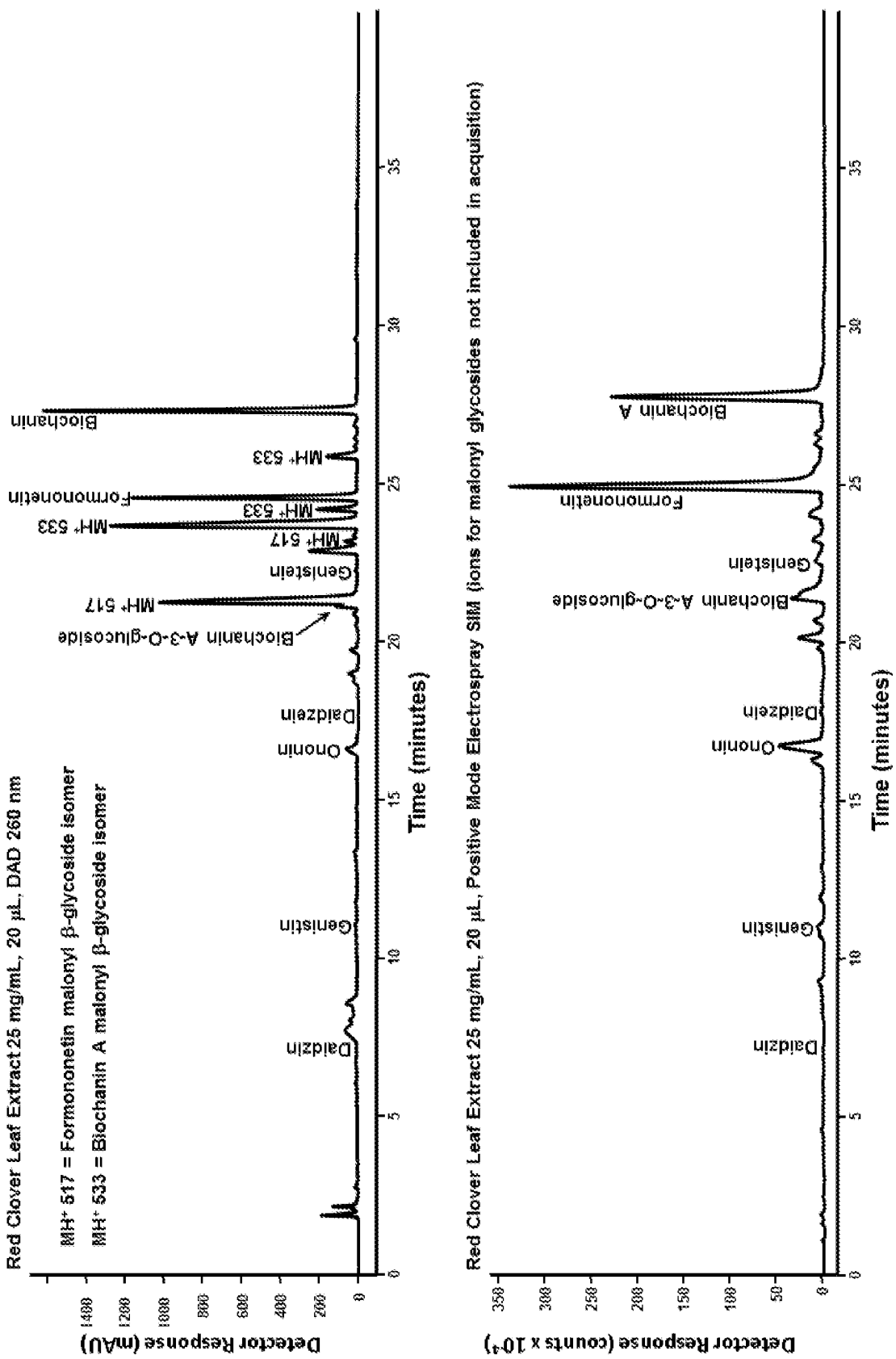
FIG. 1 shows a typical LC/MS chromatogram showing the composition of a Red clover extract.

A chromatographic analysis showed that the major ingredients in these extracts are the glucosides of formononetin and Biochanin A and their respective aglycones (FIG. 1). Tiny amounts of genistein, daidzein and their glycosides were also found. These data are consistent with what is reported in the literature (Krenn, Unterrieder et al. 2002).

A study of the stability of the key components of a Red clover extract in artificial gastric and intestinal juice showed that the glucosides were partially (<25%) converted to their respective aglycones.

According to the literature, formononetin and Biochanin A are de-methylated by the intestinal micro flora to produce two active metabolites daidzein and genistein, respectively (Hur and Rafii 2000). However, the importance of this metabolic pathway at this site is questioned (Tolleson, Doerge et al. 2002). To understand the relative importance of fecal metabolism, the metabolic rate of red clover phytoestrogens was measured.

Fresh human fecal samples were collected from 4 volunteers. Five grams of each were pooled together and mixed well with 30 mL BHI culture medium. The fecal suspension was centrifuged at 200 g for 5 min and supernatant was decanted and centrifuged at 5,000 g for another 30 min. The resultant precipitate was re-suspended with 10 mL BHI medium to produce intestinal micro flora solution.

As the biotransformation of drugs by human intestinal bacteria was determined in a 5 mL incubation system containing 250 µL intestinal microflora solution, 50 µL stock solution in DMSO in BHI medium. The incubation system was anaerobically incubated at 37° C. in a GasPak™ EZ Anaerobe Pouch System for 0 h, 24 h, 72 h, and 120 h for red clover isoflavones (the final concentrations for Biochanin A, daidzein, equol, formononetin, and genistein were 100 µM each). Zero-minute incubations served as controls. Reactions were stopped by extracting samples with 15 ml of ethanol twice. The two ethanol extractions were combined, dried and re-suspended in 80% methanol for HPLC/MS analysis.

Figure 2:
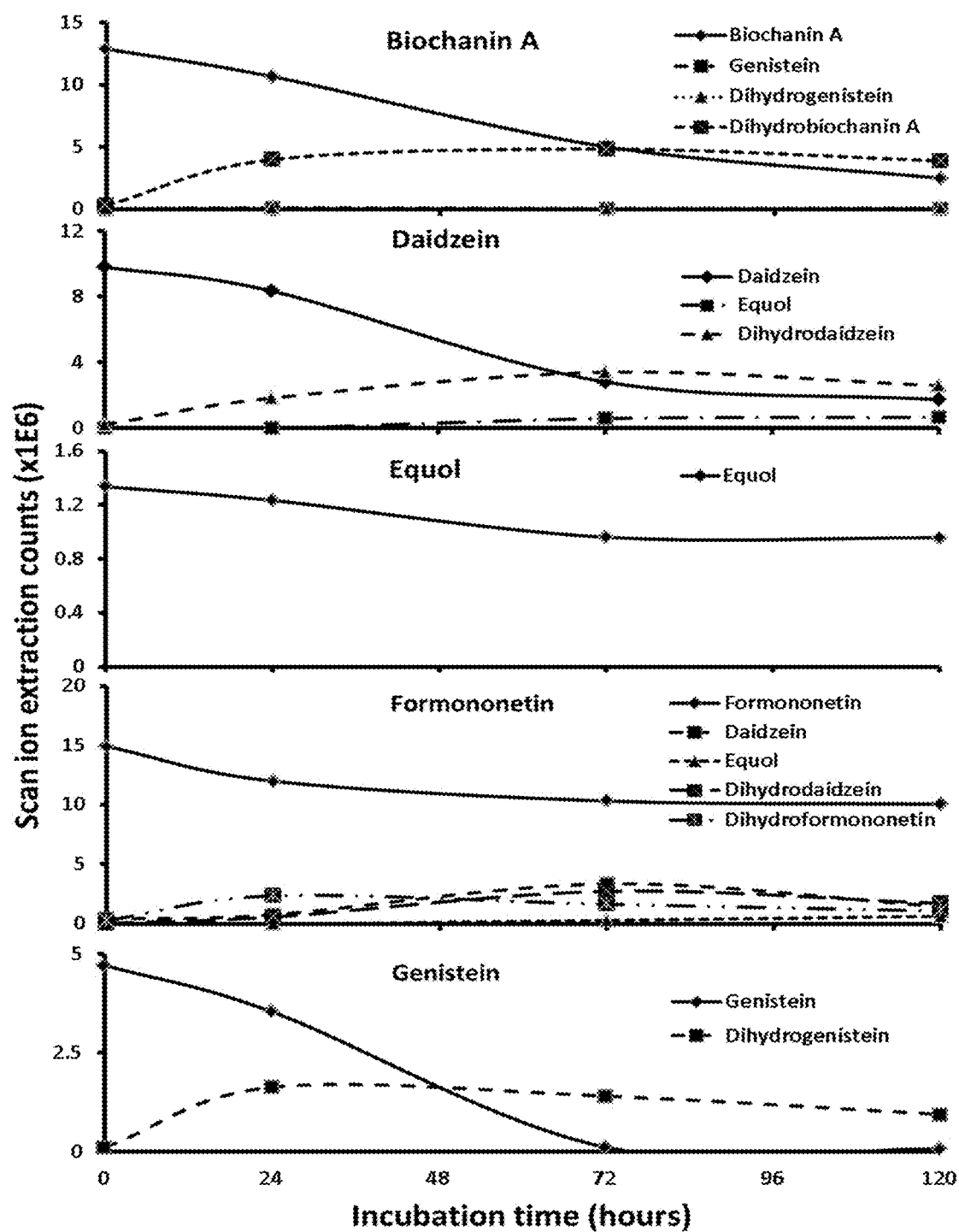
FIG. 2 shows the metabolism of the isoflavone mixtures by human fecal bacteria.

Red clover isoflavones are shown to be metabolized extensively by human intestinal microflora (FIG. 2). When Biochanin A was incubated with intestinal microflora, dihydrobiochanin A, genistein, and dihydrogenistein were formed. Daidzein was metabolized into dihydrodaidzein, and equol. Equol was the most resistant to bio-transformation. At the end of 120 hours, there was still over 60% of equol left in the incubation media, while there were less than 5% of Biochanin A, daidzein, and genistein left. The biotransformed products of equol were not identified in this study. Formononetin was biotransformed into dihydroformononetin, dihydrodaidzein, daidzein, and equol. At the end of 120-hour incubation, there was over 20% of formononetin remained. Genistein was bio-transformed into dihydrogenistein.

This set of studies clearly showed that extensive Phase I metabolism occurs in the lower part of the intestinal lumen.

Red clover extracts were subjected to permeability measurements using Caco-2 and MDCK cells. Permeability across these barriers provides an indication of absorbability.

The permeability values of formononetin, Biochanin A, daidzein and genistein are quite high, suggesting that these components are highly absorbable (Table 1). Equol has also been shown to be absorbable. However, the glucosides of the aglycones such as Biochanin A glucoside and ononin have poor permeability suggesting the bioavailability of the sugar conjugates are poorly absorbed. These results are consistent with that reported in the literature in that when these glycosides are administered to either animals or humans, no glycosides could be detected in the blood stream (Setchell, Brown et al. 2002).

TABLE 1

CaCo-2 permeability of isoflavone in a Red clover extract

| Isoflavones | Mean Peff, cm/sec | STDEV |
| --- | --- | --- |
| Biochanin A glucoside | 1.64E–08 | 1.11E–09 |
| Biochanin A | 1.08E–05 | 3.83E–07 |
| Daidzein | 2.66E–05 | 1.11E–06 |
| Daidzin | 5.36E–07 | 8.30E–08 |
| Formononetin | 2.20E–05 | 6.85E–07 |
| Genistein | 2.75E–05 | 1.22E–06 |
| Genistin | 3.46E–07 | 9.20E–08 |
| Ononin | 1.22E–07 | 1.93E–08 |

The results from the permeability study show that it would be beneficial to convert all the glucosides to their respective aglycones. Two advantages of adopting this strategy: a. the variability in the rate and extent of conversion from glucosides to aglycones between subjects will be removed. A more consistent pattern of aglycone absorption is anticipated. b. dosage calculation for the bioactives will be reduced to the aglycones only. This simplifies the standardization process.

An optimal extract of Red clover should consist of the aglycones only. An enzymatic or chemical conversion of the glucosides to their respective aglycones prior to extraction will be desirable. This can be accomplished using the literature methods (Tsao, Papadopoulos et al. 2006).

Example 2

The objectives of this example are to evaluate gut and liver metabolism of Biochanin A, formononetin, daidzein, genistein and equol. Parameters obtained from these studies are used for estimating the pharmacokinetics of these five components.

Human liver microsomes, intestinal microsomes, and hepatocytes of human female origin were purchased from XenoTech. All chemicals were purchased from Sigma-Aldrich. Isoflavones (biochanin A, daidzein, equol, formononetin, and genistein) were first dissolved in DMSO and then mixed according to a randomized table, consisting of 60 samples. The final DMSO in buffer or media was kept at 0.1%. Protocols supplied by XenoTech Inc., the supplier, were used for glucuronidation with microsomal incubation, and hepatocyte incubation. Samples were analyzed using LC/MS.

Figure 3:
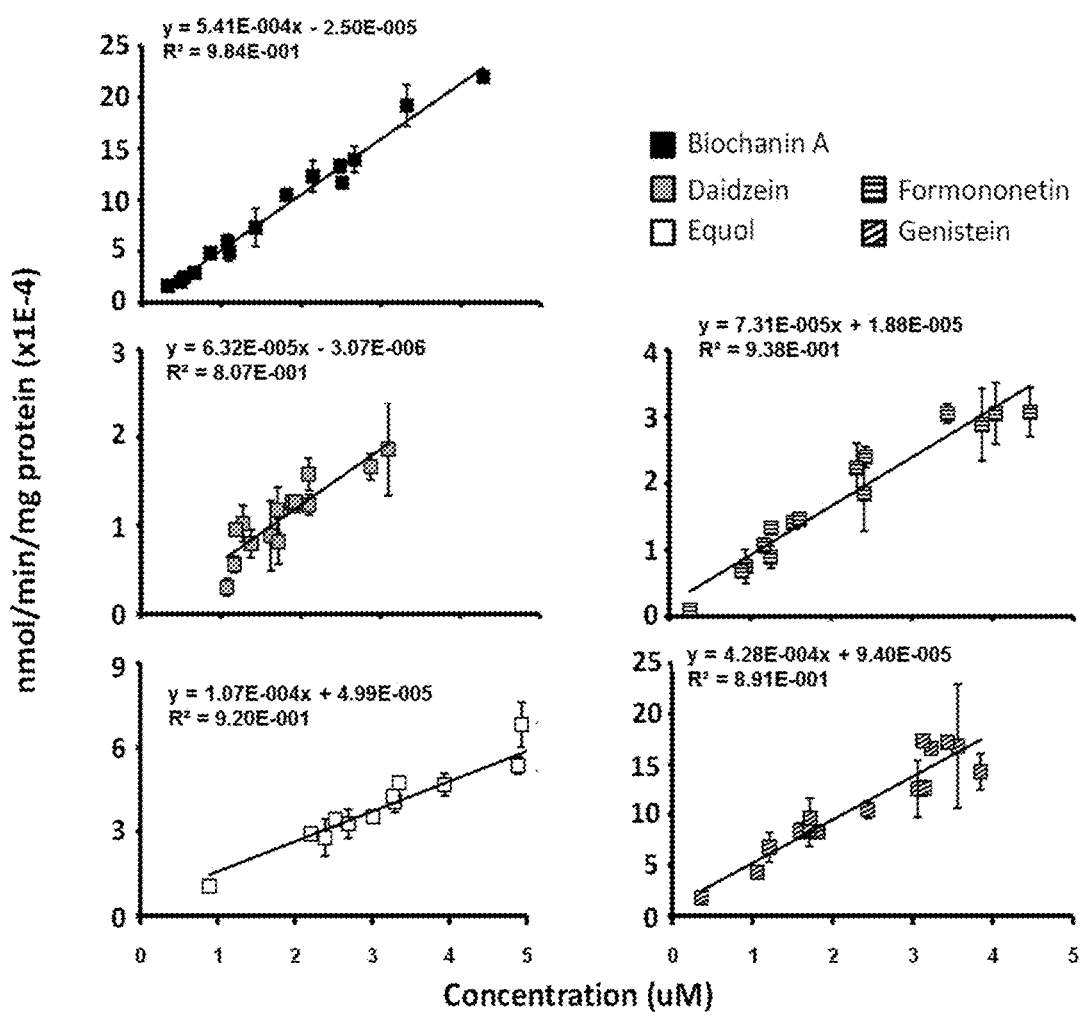
FIG. 3 shows the metabolism of the isoflavone mixtures by human intestinal microsomes.

FIG. 3 shows that metabolism of the mixtures by human intestinal microsomes: Biochanin A (5.41E-4 ml/min/mg protein)>genistein (4.28E-4 ml/min/mg protein)>equol (1.07E-4 ml/min/mg protein)>daidzein (6.32E-5 ml/min/mg protein)>formononetin (7.31E-5 ml/min/mg protein).

Figure 4:
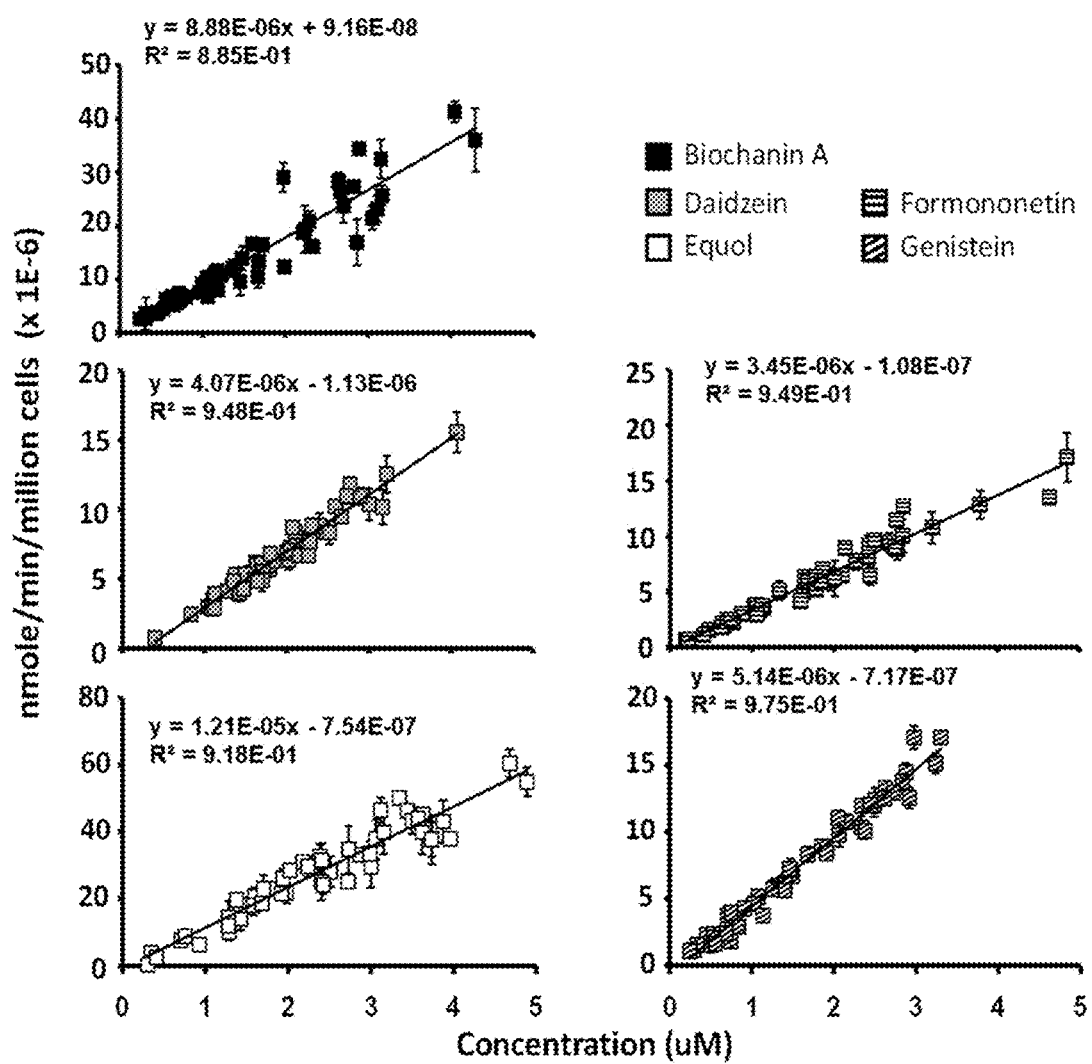
FIG. 4 shows the metabolism of the isoflavone mixtures by human hepatocytes.

FIG. 4 shows the rate of metabolism of the mixtures by human hepatocytes. The rates are: equol (1.21E-5 ml/min/million cells)>biochanin A (8.88E-6 ml/min/million cells)>genistein (5.14E-6 ml/min/million cells)>daidzein (4.07E-6 ml/min/million cells)>formononetin (3.45E-6 ml/min/million cells).

From these studies, it is clearly shown that there are no metabolic interactions between the five components. In these metabolic studies, no Phase I metabolites were detected suggesting that the formation of Phase I metabolites, such as daidzein and genistein are formed in the intestinal lumen (Example 1). This piece of information is important in that the rate of formation of these metabolites is dependent on the solubility of formononetin and Biochanin A. These results are consistent with that reported by Howes et al (2002) in that the peak time of the Phase I metabolites is delayed.

Example 3

The objective of this study is to evaluate topical bioavailability of Biochanin A, genistein, daidzein and formononetin in silico (www.cdc.gov/niosh/topics/skin/finiteskinpermcalc). Values of vapor pressure required for the calculations were obtained from website www.thegoodscentscompany.com/episys/ep1504451 for formononetin, website www.thegoodscentscompany.com/episys/ep1223481 for biochanin A, website huikephytopharm.en.hisupplier.com/product-1881573-Factory-Supply-Natural-Soybean-Extract-Daidzein for daidzein and website www.lookchem.com/Genistein/ for genistein. The following are the estimated permeability and bioavailability values of these four isoflavones:

TABLE 2

Topical permeability and bioavailability of formononetin, Biochanin A, daidzein and genistein

| | Permeability cm/s | Bioavailability % |
| --- | --- | --- |
| Formononetin | −6.42 | 96.49 |
| Biochanin A | −6.34 | 98.93 |
| Daidzein | −6.58 | 63.75 (36.16) * |
| Genistein | −6.52 | 54.02 (45.92) * |

* Value in bracket is the percentage absorbed into stratum corneum

In general, the absorption of biochanin A and formononetin is practically complete. The absorption values of genistein and daidzein are 64% and 54%, respectively. Provided a proper dosage form is designed, the bioavailability of biochanin A and formononetin could be complete and that of genistein and daidzein are 50% and 60%, respectively.

Example 4

The objectives of this study are to evaluate the effects of individual isoflavones of Red clover and their combinations on osteoblast and osteoclast differentiation.

Materials and Methods

Effects of isoflavones on the differentiation of osteoblast in MC3T3 cells followed Ge et al., 2006 and osteoclast differentiation in Raw264.7 cells followed Garcia Palacios et al., 2005. Cell numbers were measured with CellTag from Li-Cor Biosciences. Both activities of alkaline and acid phosphatase were measured with a plate reader at 405 nm.

Isoflavones were first dissolved in DMSO and stock solutions were prepared at 10 mM and the final concentration of total isoflavones in test solution was 10 µM.

Osteoblast and osteoclast differentiations were quantified by measuring activities of alkaline phosphatase (ALP) and acidic phosphatase (ACP). ALP is highly expressed by the mature osteoblasts and ACP is expressed by osteoclasts. Values of integrated intensity of fluorescence from Celltag staining serve as a correction factor for the difference in cell numbers. Therefore, ALP/cell number and ACP/cell number ratios are used to quantify osteoblast and osteoclast activities.

Results

Osteoblast Differentiation

Confluence MC3T3 cells were treated with 10 µM of isoflavones for 1 week and then the activity of alkaline phosphatase (ALP) was measured as an indicator of differentiation. Although the difference among isoflavone treatments was not significant, cells treated with Biochanin A consistently showed the highest ALP activity (FIG. 5). To examine if there were any synergistic effects, two isoflavones were mixed in a 1:9 ratio and tested in the final concentration of 10 µM. Mixtures with higher ratios (90%) of biochanin A were usually more effective in enhancing the osteoblast differentiation of MC3T3 cells than individual isoflavones alone or their combinations. In the example shown here cells treated with daidzein:Biochanin A (1:9) and genistein:Biochanin A (1:9) had higher ALP activities than Biochanin A alone (FIG. 6). To examine the effect of genistein:Biochanin ratio on osteoblast differentiation, genistein was mixed with an increased concentration of Biochanin A (an increment of 10%). With the increased concentration of Biochanin A, the differentiation enhancing ability of the mixture increased and then dropped off when the mixture only contained Biochanin A (FIG. 7).

Osteoclast Differentiation

Raw246.7 cells were treated with MCSF and RANKL to stimulate the differentiation of osteoclasts. Isoflavones were added at the final concentration of 10 µM to examine their ability to inhibit differentiation. Cells treated with Biochanin A and mixtures of Biochanin A and genistein, daidzein or formononetin at a 9:1 ratio showed the highest inhibition in osteoclast differentiation (FIG. 8). It is also noted that pure genistein and daidzein have the opposite effects in stimulating osteoclast differentiation as compared to the inhibiting effects observed in pure Biochanin A.

Conclusions

Contrary to its low estrogenicity (Beck, Unterrieder et al. 2003), Biochanin A is found to be most effective in enhancing the differentiation of osteoblast and to inhibit the differentiation of osteoclasts. Mixtures of Red clover aglycones containing high proportions of Biochanin A show synergistic effects. In one embodiment, the preferred ratios of the components at the site of action are 80 to 90% of Biochanin A, up to 15% genistein, and no more than 10% each of daidzein and formononetin.

The 9:1 concentration ratio of Biochanin A to genistein, daidzein or formononetin described herein is believed to provide desired "estrogen-like" activity that could modulate or prevent climacteric or postmenopausal symptoms. The beneficial effects of this 9:1 ratio are thus not limited to the effects on bone cells or bone-related conditions, but also on symptoms or conditions directly or indirectly related to estrogens.

Example 5

The protocol used by (Moon, Sagawa et al. 2006) was used for measuring plasma protein binding of the absorbable aglycones. Parameters have been used for PBPK simulation. Conjugates of Biochanin A, formononetin, Genistein, Daidzein and Equol are predominant components in plasma. The respective aglycones constitute less than 5% of the total concentration. Plasma protein binding of biochanin A, formononetin, genistein and equol are over 97% and daidzein was approximately 80%.

Example 6

The objectives of this study are: 1. To evaluate solubility interactions among the four phytoestrogens, which are native to Red clover, namely, Biochanin A, formononetin, daidzein and genistein; 2. To evaluate potential differences in physicochemical properties of extracts containing the same amounts of phytoestrogens.

Materials and Methods

Interactions Among Isoflavones

Isoflavones: daidzein, genistein, formononetin and Biochanin A were obtained from Indofine. Simulated intestinal fluid buffer powder mimicking a fasted state (FaSSIF) was obtained from Biorelevant SIF media, Biorelevant.com, Switzerland.

To prepare accurate concentrations of isoflavones in microtubes, stock solutions of individual isoflavones were prepared at 1 mg/mL in methanol. The amount of isoflavone designated to be held constant was provided at a concentration that well exceeded (about 20×) the saturation concentration for that isoflavone. The appropriate amount of stock was transferred to each microtube and the material was dried down in a vacuum centrifuge.

In the case of Biochanin A competition with other flavones (daidzein, genistein and formononetin), the amount of Biochanin A was held constant at 200 µg in 1 ml buffer (saturation concentration for Biochanin A in FaSSIF is about 8 µg/mL). The competing isoflavone was prepared at 0, 1, 5, 10, 50, 100, 200 µg/mL (FIGS. 11 and 12) and, in the case of formononetin, 400 µg/mL (FIG. 9).

In the case of formononetin competition with Biochanin A, the amount of formononetin was held constant at 50 µg in 1 ml buffer (saturation concentration for formononetin in FaSSIF is about 2 µg/mL). The competing Biochanin A was prepared at 0, 1, 5, 10, 50, 100 and 200 µg/mL (FIG. 10).

Each tube was then reconstituted with 1 mL of FaSSIF buffer, sonicated and allowed to equilibrate with occasional agitation for 24 hours at 37° C. This produced a solution that contained saturated isoflavone concentrations mimicking mammalian intestinal conditions.

At the end of 24 hours each tube containing isoflavones and FaSSIF buffer was briefly centrifuged at 5000 rpm in a microcentrifuge held at 37° C. (2 minutes). A portion of the supernatant (400 µL) was then immediately placed in a centrifugal filter unit (UltraFree-MC-GV 0.22 µM) and the sample filtered by centrifugation (8000 rpm, 5 minutes, 37° C.). Upon filtration 200 µL filtrate was immediately placed in a microtube and 200 µL methanol added to ensure that the isoflavones remained in solution. The sample was mixed and 200 μL of the mixture was transferred to injection vials provided with 200 μL polypropylene injection inserts.

The samples were analyzed by HPLC with diode array detection at 260 nm using 20 μL injections.

Results

When Biochanin A was placed in media representing fasted digestive juice at a concentration of 200 μg/mL at 37° C. (an amount about 25 times the soluble saturation value) the amount in solution was determined to be about 7.1 μg/mL (FIG. 9). As formononetin is introduced, Biochanin A saturation concentration dropped in a dose dependent manner and was reduced to about 4.5 μg/mL in the presence of 400 μg/mL formononetin (FIG. 9).

When the experiment was done holding formononetin at 50 μg/mL (about 25 times formononetin's saturation solubility in fasted media), increasing concentrations of Biochanin A did not affect the saturation concentration of Formononetin (FIG. 10). It is concluded that the presence of Biochanin A does not influence the saturation concentration of the much less soluble formononetin.

In experiments where Biochanin A solubility was investigated in the presence of varying concentrations of genistein, a different set of results was obtained. When Biochanin A is placed in media representing fasted digestive juice at a concentration of 200 μg/mL at 37° C. the amount in solution was determined to be about 10.8 μg/mL (FIG. 11). As genistein was introduced, Biochanin A saturation concentration increased in a dose dependent manner and reached about 24.2 μg/mL in the presence of 200 μg/mL genistein (FIG. 11). It is concluded that the solubility of Biochanin A is enhanced by the presence of genistein in fasted digestive medium.

In experiments where Biochanin A saturation solubility was investigated in the presence of varying concentrations of daidzein, a set of results different from both the formononetin and genistein experiments were obtained. When Biochanin A was placed in media representing fasted digestive juice at a concentration of 200 μg/mL at 37° C. the amount in solution was determined to be about 10.0 μg/mL (FIG. 12). As daidzein was introduced, the Biochanin A saturation concentration remains unaffected and was about 8.7 μg/mL in the presence of 200 μg/mL daidzein (FIG. 12). It is concluded that the solubility of biochanin A is unaffected by the presence of daidzein in fasted digestive media.

This set of studies clearly showed that interactions among isoflavones are not predictable. The solubility of Biochanin A in simulated intestine juice is reduced by formononetin, enhanced by genistein, and not affected by daidzein.

Similar results are obtained when simulated intestinal juice mimicking the fed state was used (data not shown).

Solubility of Isoflavones in Red Clover Extracts

Two Red clover extracts containing 40% total isoflavones were examined: Shaanix Tianzun BN 078201205123 and Acetar TYR081023.

One gram extract was placed in a disposable 12 mL glass screw top test tube. 10 mL of 100% methanol was added and the tube was capped. The tube was mixed and placed in an ultrasonic water bath for 5 minutes. The tube was then shaken every 15 minutes for 1 hour. Mixing was done at room temperature. At the end of the 1-hour incubation the tube was centrifuged (Eppendorf 5804 R, 1500 rpm, 10 minutes) and the supernatant was collected and set aside. Another 10 mL of methanol was introduced to the tube on top of the sediment and the material was sonicated, mixed and incubated as described above. This process was repeated such that 12 washes from the material were collected. The precipitate from the final wash was re-suspended in methanol.

A 100 μL aliquot collected from each 10 mL wash was diluted 1:10 with 80% methanol, centrifuged and the supernatant analyzed by HPLC with diode array detection at 260 nm using 5 or 20 μL injections. 20 μL injections were used for later washes (wash 6-12) in which daidzein, genistein and Biochanin A concentrations were much lowered.

The remaining wash supernatants as well as the re-suspended final residue were individually dried down in pre-weighed microtubes to provide an estimate of solid weight recovered in each wash.

An estimate of isoflavone concentrations in the original extracts was made by dissolving the extracts at 1 mg/mL in 80% methanol with warming and sonication. An aliquot was diluted 1:10 with 80% methanol and centrifuged. A 5 μL injection was analyzed by HPLC.

The two 40% isoflavone products extract (Acetar and Shaanxi) are found to be different from each other. There was a difference in appearance between the two 40% extracts as one has a dark green-gray color (Acetar) and the other one is off white (Shaanxi) after extraction with methanol.

The Acetar extract did not release isoflavones as rapidly when compared to that of Shaanix (Comparing FIGS. 13 and 14). Biochanin A was still being extracted after 12 sequential extracts. It appears that something in the Acetar extract is binding the isoflavones and only slowly releasing them into the methanol (FIG. 14).

The results of this study clearly showed that isoflavones from different Red clover extracts produced using different procedures could have vastly different solubility. Since absorption of isoflavones is highly dependent on their solubility, isoflavones prepared from sources or materials with identical labels may have different bioavailability. This may in part explain the inconsistent clinical results reported in the literature (Booth, Piersen et al. 2006).

The hypothesis that solubility may be an issue of phytoestrogen absorption was tested by examining the dissolution profile of a commercially available Red clover product, PROMENSIL® (30 tablets in a box, Lot #[B] 48449, Exp. March 2011).

FIG. 15 shows that the dissolution of phytoestrogens in the product is not complete, lending evidence to support the idea that an inappropriately formulated product will perform erratically because of absorption issues. It should also be pointed out that the phytoestrogens in PROMENSIL® consist of both aglycones and their glucosides. Compounding the bioavailability issue, both of these species are not completely dissolved under the experimental condition studied.

Example 7

One of the objectives of this example is to employ the proprietary pharmacodynamic/pharmacokinetic (PBPK) model to simulate the pharmacokinetic behavior of the active phytoestrogens in Red clover. Another objective of this example is to design effective formula and dosage forms of phytoestrogen products based on the simulation results and in vitro studies of the present invention.

Simulation Using Proprietary PBPK Model

Results from Examples 1, 2 and 5 are used as inputs into the proprietary PBPK model to simulate plasma concentration profiles of the four phytoestrogens: Biochanin A, formononetin, daidzein and genistein and their Phase II metabolites.

Using the parameters generated in Examples 1, 2 and 5, the proprietary PBPK model was adapted to describe the pharmacokinetics of Red clover isoflavones. The proprietary PBPK model was first validated using the clinical data of Howes et al. (2002). The model was considered validated when the simulated results of Area Under the Curve (AUC) values of the Phase II metabolites are agreeable (within 2-fold, Table 3, second and third column) with that published by Howes et al. (2002).

After the validation of the proprietary PBPK model, the resultant PK data were used to estimate other PK data, dose and routes of administration. In one embodiment, the PBPK model was used to simulate the AUC values of isoflavones after oral and intravenous administration (Table 3, fourth and fifth column).

higher than that of a comparative oral dose (Table 3). This suggests that non-oral dosage could be as low as 0.2 to 3% of that of oral doses.

High variability, low bioavailability and solubility limited absorption are the major causes for therapeutic failure. In a recent review (Lagari and Levis 2014), it was reported that there was a much higher proportion of clinical trials showing Red clover phytoestrogens were ineffective in treating post-menopausal bone loss and climacteric symptoms than the effective ones. Dosages used for clinical trials went as high as 80 mg total phytoestrogens. Based on the literature reports and observations made in this invention, plasma concentrations of biochanin A and genistein measured by Howes et al. (2002) are considered to be marginally effective since the total phytoestrogen dose used by Howe et al was 87 mg.

Based on the results described in this invention, failure of Red clover therapy is not surprising because low solubility,

TABLE 3

Comparison of plasma levels of isoflavones obtained from clinical samples and simulation results using the PBPK model

| | $AUC_{0-24}$, ng * h/mL | | | | Estimated Parameters | |
|---|---|---|---|---|---|---|
| | Phase II metabolites | | Aglycones | | Aglycones | |
| | Howes' | | (simulation) | | | Clearance |
| | data[#] | Simulation | Oral | IV | Bioavailability % | ml/min |
| Formononetin | 112 ± 35 | 123 | 9.47 | 1989 | 0.48 | 268 |
| Biochanin A | 518 ± 518 | 519 | 4.99 | 2422 | 0.21 | 337 |
| Daidzein | 891 ± 135 | 693 | 7.49 | 261 | 2.87 | 192 |
| Genistein | 1463 ± 115 | 1231 | 3.85 | 229 | 1.68 | 218 |

[#]Data reported by Howes et al. (2002). Two Promensil tablets contain 32 mg of Formononetin, 49 mg of Biochanin A, 3 mg of daidzein and 3 mg of genistein. Based on the maximum plasma concentration (Cmax) in ng/mL reported by Howes et al. (2002), the maximum plasma concentration in μM was calculated: 0.042 μM for Formononetin, 0.168 μM for Biochanin A, 0.423 μM for daidzein and 0.247 μM for daidzein.

Clinical data of Howes et al. (2002) indicated that the plasma isoflavone levels in humans are highly varied (See C. of Table 1 of Howes et al.). The huge variation of plasma isoflavone levels observed could be due to high first-pass metabolism, lack of solubility and solubility interactions among isoflavones. The solubility issues would pose an upper limit of isoflavone absorption, preventing the achievement of a higher plasma concentration.

Howes et al's (2002) data also showed that AUC values among subjects are highly variable (>10 fold). This variation can be explained by the instability of glucosides, low solubility of the aglycones, interaction among aglycones at the solubility level, aglycone metabolism of the aglycones by colonic bacteria and high first-pass gut and liver metabolism.

Limited solubility of phytoestrogens in the small intestine may be responsible for the lack of a dose-dependent increase in clinical response to Red clover isoflavones (Booth, Piersen et al. 2006).

Comparing the AUC values of phytoestrogens obtained after intravenous administration and oral administration, it is observed that the estimated AUC values of aglycone obtained after intravenous administration is approximately 35 to 500 times higher than those after oral administration (Table 3, fourth and fifth column).

This simulation suggests that bioavailability of phytoestrogens could be enhanced by administering the compounds via non-oral route. For example, after intravenous administration, AUC of phytoestrogens could be 35 to 500-fold high first-pass effects and variable colonic metabolism are key factors which lead to low bioavailability and high inter-individual variability of the phytoestrogens.

The dosages of total phytoestrogens used in clinical trials are typically as high as 80 mg but could only achieve low AUC values of the isoflavones, hence limiting the therapeutic efficacy of the products. The present simulation data (not shown) indicates that AUC of individual isoflavone would not increase with the increasing oral dose because of the limited solubility and first-pass metabolism. That is, dosages higher than 80 mg are not likely to further enhance the therapeutic efficacy. These results are consistent with that reported by Booth et. al. (2006), who showed that the efficacy of phytoestrogens was not dose-dependent.

Hence, to deal with the limited efficacy of phytoestrogen products, one of the objectives of the present invention is to account for the pharmacokinetic properties of the isoflavones and to design effective isoflavone products with optimal dosage forms and dose ratios of the isoflavones.

Table 4 shows one example of how the present invention designs a Red clover composition for topical administration based on the simulation results, that is, in view of the pharmacokinetic and the pharmacodynamic properties of the components. In this example, the target AUC to be achieved for biochanin A by the topically administered Red clover composition is defined at 10 times of the AUC value obtained after the oral administration of the composition ($AUC_{Oral}$). The target AUC ratios for biochanin A: genistein is 9:1, biochanin A: formononetin is 20:1 and biochanin A:

daidzein is 20:1. For each isoflavone, the topical dose is calculated based on the target AUC value as calculated and the AUC value obtained after intravenous administration as simulated ($AUC_{IV}$). Since $AUC_{IV}$ takes into account of 100% absorption of the component and clearance from the body, a calculation of topical dose based on $AUC_{IV}$ would provide a good estimation if the component is 100% absorbed after administration, otherwise normalization is required to account for the lesser extent of absorption. The present simulation results showed that Biochanin A and formononetin are 100% absorbed while genistein and daidzein are 54.02 and 63.75%, respectively (Table 2). Hence, the estimated topical dose of formononetin, daidzein and genistein were calculated based on specified ratios as inferred from the simulation data (Table 4).

simulation (See Table 5). In one embodiment, the dose ratio of Biochanin A to genistein is extrapolated to about 2:1 to 30:1. In another embodiment, the dose ratio of Biochanin A to formononetin is extrapolated to about 5:1 to 100:1. In another embodiment, the dose ratio of Biochanin A to daidzein is extrapolated to about 5:1 to 90:1.

In one embodiment of the present composition which comprises at least 80% of Biochanin A, at least 1% of genistein, no more than 5% of formononetin and no more than 5% of daidzein, the ratios of isoflavones are: about 4:1 to 99:1 of Biochanin A to genistein, about 16:1 to 100:1 of Biochanin A to formononetin, and about 16:1 to 90:1 of Biochanin A to daidzein. Dose ratios for other doses of isoflavones can be deduced similarly.

TABLE 4

Extrapolated topical doses of four isoflavones and their AUC

| | $AUC_{0-24}$, ng * h/mL Aglycones (simulation) | | Molecular weight | Target AUC (ng * h/mL)* | Topical** dose (mg) | % of total topical dose | Dose ratio of Biochanin A:isoflavone |
|---|---|---|---|---|---|---|---|
| | Oral | IV | | | | | |
| Biochanin A | 4.99 | 2422 | 284.26 | 49.9 | 1.01 | 82.13 | 1 |
| Formononetin | 9.47 | 1989 | 268.26 | 2.50 | 0.04 | 3.27 | 25.15 |
| Daidzein | 7.49 | 261 | 254.33 | 2.50 | 0.045 | 3.66 | 22.44 |
| Genistein | 3.85 | 229 | 270.241 | 5.54 | 0.134 | 10.94 | 7.51 |
| | | | | Total dose | 1.23 | 100 | / |

*For Biochanin A, the target AUC is 10 times the AUC value of orally taken Biochanin A. Target AUC of formononetin, daidzein and genistein were calculated based on the following ratios - Biochanin A:formononetin (20:1); Biochanin A:genistein(9:1); and Biochanin A:daidzein (20:1).
**Dosages could be as low as estimated assuming optimal absorption.

The data in Table 4 shows that when the composition is formulated for topical administration, the total dosage of phytoestrogens could be as low as 1.23 mg, which is extremely low compared to the common dosage 80 mg for oral administration. The topical dosage form minimizes the problems of limited solubility and first-pass metabolism, and hence significantly enhances the bioavailability and therapeutic efficacy of the products.

In the example provided by Table 4, the dose ratio of Biochanin A to formononetin, daidzein and genistein are about 25:1, 22:1 and 8:1 respectively. Hence, in one embodiment, the present composition is formulated to include the four isoflavones in the following ranges of ratios: Biochanin A to formononetin of about 20:1 to 30:1, Biochanin A to daidzein of about 18:1 to 30:1, and Biochanin A to genistein of about 6:1 to 9:1.

In one embodiment, doses of components to be administered to a subject are adjusted not only in view of the pharmacokinetic and pharmacodynamic properties of the components but also in a way that accounts for any variability in the simulation data in order to achieve a desired ratio of components at the site of action. In the present study, a two-fold variability in the results of simulation is expected and taken into account for designing the formulation of the present compositions. Therefore, based on the formulation in Table 4, the dose of the four isoflavones and their dose ratios can be translated to other doses and ratios accounting for the two-fold variation in the clinical data and in the

TABLE 5

Extrapolation of topical doses and dose ratios of four isoflavones

| | Target AUC (ng*h/mL) | Range of target AUC* (ng*h/mL) | Range of dose of isoflavones (mg) | Dose ratio of Biochanin A:isoflavone⁺ |
|---|---|---|---|---|
| Biochanin A | 49.9 | 24.95-99.80 | 0.50-2.02 | 1 |
| Formononetin | 2.50 | 1.25-4.99 | 0.02-0.08 | 6.29-100.60 |
| Daidzein | 2.50 | 1.25-4.99 | 0.022-0.090 | 5.61-90.00 |
| Genistein | 5.54 | 2.77-11.09 | 0.07-0.27 | 1.88-30.03 |

*Range of target AUC is taken as 50-200% of the target AUC value.
⁺Lower limit of dose ratio = lowest dose of Biochanin A/highest dose of isoflavone; Upper limit of dose ratio = highest dose of Biochanin A/lowest dose of isoflavone.

Consideration of In Vitro Efficacy and Interactions Among Isoflavones

As discussed in Example 4, the present invention discovered that the concentration ratio 9:1 of isoflavones is effective in modulating estrogen-related activity. The concentration of isoflavones used in the present in vitro studies was 10 μM. This concentration ranges approximately 20 times for genistein (10 μM/0.423 μM) to 240 times for formononetin (10 μM/0.042 μM) higher than that observed in humans (Howes et al., 2002). This difference is to be expected as the duration of study in vitro (one week) was a lot shorter than that in the clinical trials (>6 months) (Booth, 2006).

Results from the present in vitro studies (Example 4) suggest that in vivo plasma concentration ratio of biochanin A to genistein of 9:1 provides the highest efficacy. It should be noted that the ratio of the components, rather than the actual concentrations used in the in vitro studies, is more clinically relevant. In one embodiment, the 9:1 ratio of biochanin A to genistein used in Example 4 is translated to a dose ratio accounting for the higher clearance rate of biochanin A than genistein, and in view of the simulation data obtained from the proprietary PBPK model.

Commercially, it is common to find Red clover extracts containing higher proportions of formononetin. As demonstrated in the present invention, Biochanin A is found to be the most effective in modulating the differentiation of bone cells (Example 4) and formononetin is shown to lower Biochanin A's solubility in simulated intestinal fluid (Example 6). Thus it is not surprising to find that Red clover extracts containing high formononetin are ineffective.

In the realm of solubility limitations, an effective combination of Red clover phytoestrogens should contain very low levels of Formononetin (<2 to 10%).

Genistein has been found to have dual functions. It enhances the solubility of Biochanin A and acts synergistically with Biochanin A in enhancing bone remodeling.

A low percentage of daidzein and formononetin, approximately 10% of that of biochanin A (FIG. 8) has also been found to have synergistic antiresorptive effects.

Taking together, an ideal combination of Red clover phytoestrogens should contain a high content of Biochanin A (>80%) and smaller contents of genistein, daidzein and formononetin. In one embodiment, the dose ratios of these components can be adjusted in view of the above simulation data and/or the in vitro studies in Example 4.

To avoid extensive first-pass effects, solubility issues and variable colonic metabolism, an alternative route of administration other than oral should be employed. The present composition is formulated for administration via different routes in accordance with the need. In one embodiment, the present composition is formulated for administration via the following routes: parenteral such as intravenous, subcutaneous and intramuscular. In another embodiment, the present composition is formulated for administration via topical, transdermal, vaginal, buccal or sublingual administration.

In one embodiment, the dosage of phytoestrogens can be less than 0.2-10% of the normal clinical dose, which is about 80 mg. That is, the dosage of phytoestrogens used herein can be less than 0.16 to 8 mg. These low dosages should provide significantly higher plasma levels of Biochanin A, genistein, daidzein and formononetin when compared to a regular 80 mg dose of Red clover isoflavones.

Assuming an 80 mg dose is marginally active (Lagari and Levis 2014), the combination of phytoestrogens as disclosed herein would greatly enhance clinical effectiveness of Red clover phytoestrogens in treating bone loss and other climacteric symptoms.

Example 8

This example records the experience of two postmenopausal women after taking a vaginal suppository designed based on the present invention for a period 7 to 14 days. The first woman was a 55-year-old postmenopausal female who suffered from hot flashes and vaginal atrophy, but otherwise healthy. The second woman is a 64-year-old postmenopausal woman who suffered from vaginal dryness and osteoarthritis.

Vaginal suppositories containing 5 mg of biochanin A, 0.104 mg of genistein, 0.087 mg of formononetin and 0.071 mg of daidzein were prepared using a blend of polyethylene glycol (PEG) base, containing 40% PEG 300 and 60% PEG 3350 and silica gel micro. In this particular formulation, the dose ratios of isoflavones are: about 48:1 of Biochanin A to genistein, about 58:1 of Biochanin A to formononetin, and about 70:1 of Biochanin A to daidzein.

The first subject applied a suppository once a day before bedtime for six consecutive days. After the first dose, the preparation has been able to arrest the onset of hot flashes and night sweat (feeling of hotness and heavy sweating) within two hours and the symptoms did not recur during this six-day period. Vaginal dryness is reported to disappear after the third application.

Using the same dosing regimen, the symptom of vaginal dryness for the second woman disappeared on the third day. During the treatment period, vaginal dryness did not reappear.

The two studies empirically proved that the present compositions, when formulated for vaginal administration and formulated with optimal ratios of the isoflavones, generated immediate therapeutic effects in a few days. Therefore, the present invention represents a big improvement over conventional treatments which usually take several weeks to take effects and at best generate marginal therapeutic effects.

In summary, the present invention investigated the effects of different combination of isoflavones of Red clover on the differentiation of osteoblasts and osteoclasts (Example 4), studied the solubility and interactions among these isoflavones (Example 6), and analyzed the pharmacokinetic properties of these isoflavones using a proprietary physiologically based pharmacokinetic and pharmacodynamic model (PBPKPD) (Example 7). The present findings provide a basis to design compositions that are more effective in modulating climacteric symptoms while requiring a much lower dosage of Red clover phytoestrogens than conventional products available at the time of the invention. The clinical data in Example 8 proved that the present compositions are effective in treating climacteric symptoms including hot flashes, night sweat and vaginal dryness within a few days, and the daily dosage of phytoestrogens required is only about 6.6% of the conventional dosage 80 mg. In support of the data described in this invention, the present compositions, when formulated properly, could be used to modulate, prevent or treat climacteric symptoms within a short period of time.

REFERENCES

Beck, V., U. Rohr and A. Jungbauer (2005). "Phytoestrogens derived from red clover: an alternative to estrogen replacement therapy?" *J Steroid Biochem Mol Biol* 94(5): 499-518.

Beck, V., E. Unterrieder, L. Krenn, W. Kubelka and A. Jungbauer (2003). "Comparison of hormonal activity (estrogen, androgen and progestin) of standardized plant extracts for large scale use in hormone replacement therapy." *J Steroid Biochem Mol Biol* 84(2-3): 259-268.

Booth, N. L., C. R. Overk, P. Yao, J. E. Burdette, D. Nikolic, S. N. Chen, J. L. Bolton, R. B. van Breemen, G. F. Pauli and N. R. Farnsworth (2006). "The chemical and biologic profile of a red clover (*Trifolium pratense* L.) phase II clinical extract." *J Altern Complement Med* 12(2): 133-139.

Booth, N. L., C. E. Piersen, S. Banuvar, S. E. Geller, L. P. Shulman and N. R. Farnsworth (2006). "Clinical studies of red clover (*Trifolium pratense*) dietary supplements in menopause: a literature review." *Menopause* 13(2): 251-264.

Chen, J., H. Lin and M. Hu (2005). "Absorption and metabolism of genistein and its five isoflavone analogs in the human intestinal Caco-2 model." *Cancer Chemother Pharmacol* 55(2): 159-169.

Chen, J., S. Wang, X. Jia, S. Bajimaya, H. Lin, V. H. Tam and M. Hu (2005). "Disposition of flavonoids via recycling: comparison of intestinal versus hepatic disposition." *Drug Metab Dispos* 33(12): 1777-1784.

Fernandez, E., S. Gallus, C. Bosetti, S. Franceschi, E. Negri and C. La Vecchia (2003). "Hormone replacement therapy and cancer risk: a systematic analysis from a network of case-control studies." *Int J Cancer* 105(3): 408-412.

Gambacciani, M., M. Ciaponi and A. R. Genazzani (2007). "The HRT misuse and osteoporosis epidemic: a possible future scenario." *Climacteric* 10(4): 273-275.

Gambacciani, M., P. Monteleone, A. Sacco and A. R. Genazzani (2003). "Hormone replacement therapy and endometrial, ovarian and colorectal cancer." *Best Pract Res Clin Endocrinol Metab* 17(1): 139-147.

Ghazanfarpour, M., R. Latifnejad Roudsari, G. Treglia and R. Sadeghi (2015). "Topical administration of isoflavones for treatment of vaginal symptoms in postmenopausal women: A systematic review of randomised controlled trials." *J Obstet Gynaecol* 35(8): 783-787.

Ghazanfarpour, M., R. Sadeghi, R. Latifnejad Roudsari, K. Mirzaii Najmabadi, M. Mousavi Bazaz, S. Abdolahian and T. Khadivzadeh (2015). "Effects of red clover on hot flash and circulating hormone concentrations in menopausal women: a systematic review and meta-analysis." *Avicenna J Phytomed* 5(6): 498-511.

Ghazanfarpour, M., R. Sadeghi and R. L. Roudsari (2016). "The application of soy isoflavones for subjective symptoms and objective signs of vaginal atrophy in menopause: A systematic review of randomised controlled trials." *J Obstet Gynaecol* 36(2): 160-171.

Ghazanfarpour, M., R. Sadeghi, R. L. Roudsari, I. Khorsand, T. Khadivzadeh and B. Muoio (2016). "Red clover for treatment of hot flashes and menopausal symptoms: A systematic review and meta-analysis." *J Obstet Gynaecol* 36(3): 301-311.

Howes, J., M. Waring, L. Huang and L. G. Howes (2002). "Long-term pharmacokinetics of an extract of isoflavones from red clover (*Trifolium pratense*)." *J Altern Complement Med* 8(2): 135-142.

Hur, H. and F. Rafii (2000). "Biotransformation of the isoflavonoids biochanin A, formononetin, and glycitein by *Eubacterium limosum*." *FEMS Microbiol Lett* 192(1): 21-25.

Jia, X., J. Chen, H. Lin and M. Hu (2004). "Disposition of flavonoids via enteric recycling: enzyme-transporter coupling affects metabolism of biochanin A and formononetin and excretion of their phase II conjugates." *J Pharmacol Exp Ther* 310(3): 1103-1113.

Krenn, L., I. Unterrieder and R. Ruprechter (2002). "Quantification of isoflavones in red clover by high-performance liquid chromatography." *J Chromatogr B Analyt Technol Biomed Life Sci* 777(1-2): 123-128.

Lagari, V. S. and S. Levis (2014). "Phytoestrogens for menopausal bone loss and climacteric symptoms." *J Steroid Biochem Mol Biol* 139: 294-301.

Liu, J., J. E. Burdette, H. Xu, C. Gu, R. B. van Breemen, K. P. Bhat, N. Booth, A. I. Constantinou, J. M. Pezzuto, H. H. Fong, N. R. Farnsworth and J. L. Bolton (2001). "Evaluation of estrogenic activity of plant extracts for the potential treatment of menopausal symptoms." *J Agric Food Chem* 49(5): 2472-2479.

Ma, D. F., L. Q. Qin, P. Y. Wang and R. Katoh (2008). "Soy isoflavone intake inhibits bone resorption and stimulates bone formation in menopausal women: meta-analysis of randomized controlled trials." *Eur J Clin Nutr* 62(2): 155-161.

Magee, P. J. (2011). "Is equol production beneficial to health?" *Proc Nutr Soc* 70(1): 10-18.

Moon, Y. J., K. Sagawa, K. Frederick, S. Zhang and M. E. Morris (2006). "Pharmacokinetics and bioavailability of the isoflavone biochanin A in rats." *Aaps J* 8(3): E433-442.

Overk, C. R., P. Yao, L. R. Chadwick, D. Nikolic, Y. Sun, M. A. Cuendet, Y. Deng, A. S. Hedayat, G. F. Pauli, N. R. Farnsworth, R. B. van Breemen and J. L. Bolton (2005). "Comparison of the in vitro estrogenic activities of compounds from hops (*Humulus lupulus*) and red clover (*Trifolium pratense*)." *J Agric Food Chem* 53(16): 6246-6253.

Seelig, M. S., B. M. Altura and B. T. Altura (2004). "Benefits and risks of sex hormone replacement in postmenopausal women." *J Am Coll Nutr* 23(5): 482S-496S.

Setchell, K. D., N. M. Brown, L. Zimmer-Nechemias, W. T. Brashear, B. E. Wolfe, A. S. Kirschner and J. E. Heubi (2002). "Evidence for lack of absorption of soy isoflavone glycosides in humans, supporting the crucial role of intestinal metabolism for bioavailability." *Am J Clin Nutr* 76(2): 447-453.

Setchell, K. D. and A. Cassidy (1999). "Dietary isoflavones: biological effects and relevance to human health." *J Nutr* 129(3): 758S-767S.

Tolleson, W. H., D. R. Doerge, M. I. Churchwell, M. M. Marques and D. W. Roberts (2002). "Metabolism of biochanin A and formononetin by human liver microsomes in vitro." *J Agric Food Chem* 50(17): 4783-4790.

Tsao, R., Y. Papadopoulos, R. Yang, J. C. Young and K. McRae (2006). "Isoflavone profiles of red clovers and their distribution in different parts harvested at different growing stages." *J. Agric. Food Chem.* 54: 5797-5805.

Wuttke, W., H. Jarry and D. Seidlova-Wuttke (2007). "Isoflavones—safe food additives or dangerous drugs?" *Ageing Res Rev* 6(2): 150-188.

What is claimed is:

1. A pharmaceutical composition for treating one or more climacteric symptoms in a subject, comprising 1-6 mg of total red clover isoflavones per day comprising 80%-96% Biochanin A, 1%-12% genistein, 1%-5% formononetin and 1%-5% of daidzein, wherein said isoflavones are aglycone forms, the composition is configured to be administered via a route to avoid first-pass gastrointestinal and hepatic effects, and to avoid colonic bacterial metabolism, wherein the climacteric symptoms are selected from the group consisting of:
   a. hot flashes;
   b. vaginal atrophy;
   c. vaginal dryness;
   d. diaphoresis;
   e. night sweat;
   f. urinary tract symptoms; and
   g. sleep disturbance.

2. The pharmaceutical composition of claim 1, comprising 5 mg of Biochanin A, 0.104 mg of genistein, 0.087 mg of formononetin, and 0.071 mg of daidzein.

3. The pharmaceutical composition of claim 1, wherein the weight ratio of Biochanin A to genistein is about 48:1.

4. The pharmaceutical composition of claim 1, wherein the weight ratio of Biochanin A to formononetin is about 58:1.

5. The pharmaceutical composition of claim 1, wherein the weight ratio of Biochanin A to daidzein is about 70:1.

6. The pharmaceutical composition of claim 1, formulated as a dosage form for parenteral, buccal, sublingual, topical, transdermal or intra-vaginal administration.

7. The pharmaceutical composition of claim 1, formulated as a dosage form for intramuscular, subcutaneous or intravenous administration.

8. The pharmaceutical composition of claim 1, formulated in the form of a suppository, cream, injection, solution, or suspension.

* * * * *